US010393722B2

(12) United States Patent
Koshnick et al.

(10) Patent No.: US 10,393,722 B2
(45) Date of Patent: Aug. 27, 2019

(54) SOIL QUALITY MEASUREMENT DEVICE

(71) Applicant: The Climate Corporation, San Francisco, CA (US)

(72) Inventors: Nick Koshnick, San Francisco, CA (US); Phil Baurer, Tremont, IL (US); Greg Chiocco, San Francisco, CA (US)

(73) Assignee: The Climate Corporation, San Francisco, CA (US)

( * ) Notice: Subject to any disclaimer, the term of this patent is extended or adjusted under 35 U.S.C. 154(b) by 82 days.

(21) Appl. No.: 15/011,356

(22) Filed: Jan. 29, 2016

(65) Prior Publication Data
US 2016/0223511 A1 Aug. 4, 2016

Related U.S. Application Data

(60) Provisional application No. 62/110,405, filed on Jan. 30, 2015, provisional application No. 62/256,643, filed on Nov. 17, 2015.

(51) Int. Cl.
*G01N 33/24* (2006.01)
*G01N 1/08* (2006.01)
*G06Q 10/10* (2012.01)
*A01C 21/00* (2006.01)

(52) U.S. Cl.
CPC .......... *G01N 33/24* (2013.01); *A01C 21/005* (2013.01); *A01C 21/007* (2013.01); *G01N 1/08* (2013.01); *G06Q 10/10* (2013.01); *G01N 2033/245* (2013.01)

(58) Field of Classification Search
None
See application file for complete search history.

(56) References Cited

U.S. PATENT DOCUMENTS 4,445,788 A * 5/1984 Twersky ............... A01G 1/00
  374/110
6,016,713 A * 1/2000 Hale ................... A01B 79/005
  73/864.45
2016/0223511 A1 8/2016 Koshnick et al.

FOREIGN PATENT DOCUMENTS

| CN | 103196698 A | 7/2013 | |
| JP | 3932662 B2 | 6/2007 | |
| WO | WO 98/57143 A2 | 12/1998 | |
| WO | WO 9857143 A2 * | 12/1998 | ............. E02D 1/022 |
| WO | WO2012/057929 A1 | 5/2012 | |
| WO | WO 2012057929 A1 * | 5/2012 | ............. G01N 33/24 |

OTHER PUBLICATIONS

Database WPI, Week 201371, Thomas Scientific, London, BG, dated Jul. 10, 2013, 1 page.*

(Continued)

*Primary Examiner* — Steven B Gauthier
(74) *Attorney, Agent, or Firm* — Hickman Palermo Becker Bingham LLP

(57) ABSTRACT

Systems, methods and apparatus are provided for soil testing. In some embodiments, a soil sample quality criterion is determined and associated with the soil sample. In some embodiments a soil characteristic measurement is additionally taken and associated with the soil sample. In some embodiments, the soil sample and its associated data are associated with a container in which the soil sample is placed.

20 Claims, 11 Drawing Sheets

(56) References Cited

OTHER PUBLICATIONS

International Searching Authority, "Search Report" in application No. PCT/US2016/015616, dated May 9, 2016, 14 pages.
Current Claims in application No. PCT/US2016/015616, dated May 2016, 3 pages.
Claims in Chilian Patent Application No. 201701940 dated Aug. 2018, 3 pages.
Chilian Patent Office, "Office Action" in application No. 201701940, dated Aug. 22, 2018, 5 pages.

\* cited by examiner

Fig. 2
(a)
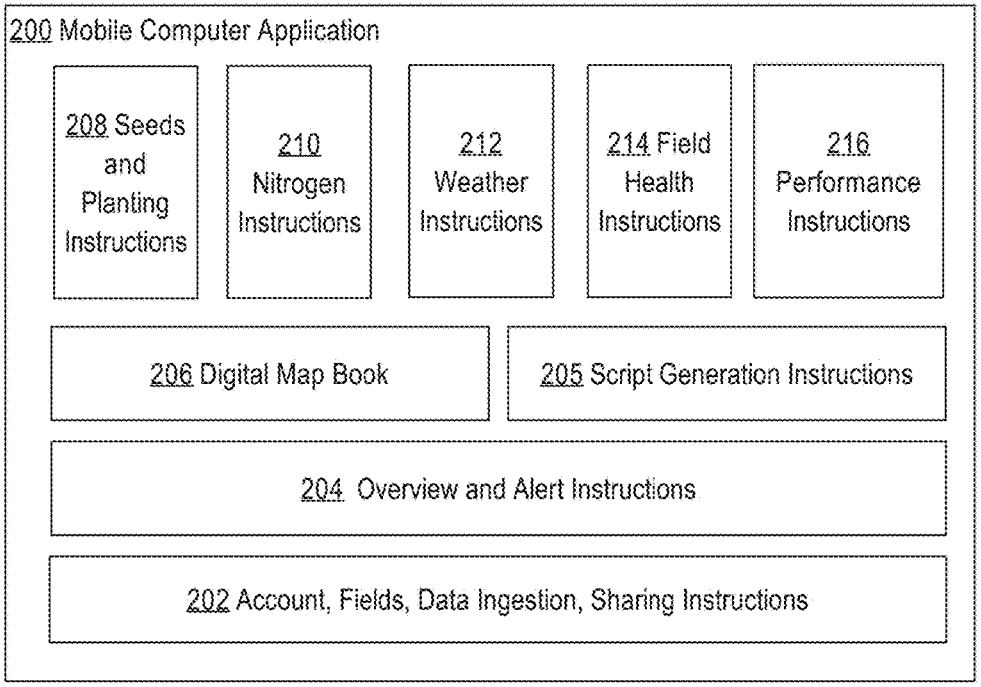
(b)
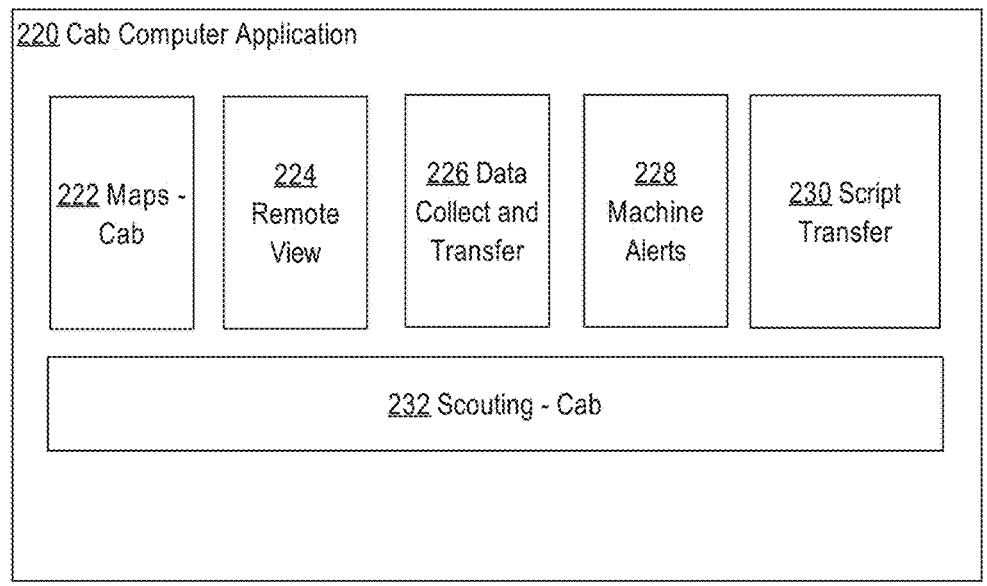

FIG. 5

Data Manager

[ Nitrogen | Planting | Practices | Soil ]

| Planting 1 (4 Fields) | Planting 2 (0 Fields) | Planting 3 (0 Fields) | Planting 4 (1 Fields) | Add New Planting Plan |
|---|---|---|---|---|
| Crop Corn Product<br>Plant Date: 2016-04-12<br>ILU 112 \| Pop: 34000<br>[Edit] [Apply] | Crop Corn Product<br>Plant Date: 2016-04-15<br>ILU 83 \| Pop: 34000<br>[Edit] [Apply] | Crop Corn Product<br>Plant Date: 2016-04-13<br>ILU 83 \| Pop: 34000<br>[Edit] [Apply] | Crop Corn Product<br>Plant Date: 2016-04-13<br>ILU 112 \| Pop: 34000<br>[Edit] [Apply] | [ + ] |

| | CROP | PLANTED ACRES | PRODUCT | RELATIVE MATURITY | TARGET YIELD | POPULATION(AVG) | PLA |
|---|---|---|---|---|---|---|---|
| ☐ Select All | | | | | | | |
| ☐ Ames, IA 1<br>Corn \| 100 \| Boone, IA | Corn | — | DMC82-M | 112 | 160 | 34000 | Apr |
| ☐ Austin, MN 1<br>Corn \| 100 \| Fredricks, MN | Corn | — | DMC82-M | 114 | 160 | 36000 | Apr |
| ☐ Boone, IN 1<br>Corn \| 100 \| Boone, IA | Corn | — | DMC82-M | 112 | 150 | 34000 | Apr |
| ☐ Champaign 1<br>Corn \| 100 \| Champaign, IL | Corn | — | — | 112 | 200 | 34000 | Apr |
| ☐ E Nebraska 1<br>Corn \| 100 \| Burt, NE | Corn | — | — | 112 | 160 | 34000 | Apr |

*FIG. 6*

SOIL QUALITY MEASUREMENT DEVICE

BENEFIT CLAIM

This application claims the benefit under 35 U.S.C. § 119(e) of provisional application 62/110,405, filed Jan. 30, 2015, and provisional application 62/256,643, filed Nov. 17, 2015, the entire contents of which is hereby incorporated by reference as if fully set forth herein.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright or rights whatsoever. © 2015-2016 The Climate Corporation.

FIELD OF THE DISCLOSURE

The present disclosure relates to soil measurement and testing methods and apparatus.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

The embodiments described herein relate generally to agricultural activities and, more particularly, systems and methods for sampling and testing soil at locations in an agricultural field or other location of soil.

Soil sampling and testing is often carried out by manually obtaining soil cores from multiple locations in a field. Existing solutions for obtaining soil cores simply enable the user to obtain a core of the correct size. However, the existing solutions fail to enhance sample consistency and record-keeping.

Accordingly, there is a need in the art for improved systems, methods and apparatus for soil testing. Such improved methods and systems may enhance sample consistency and record-keeping associated with each sample.

SUMMARY

The appended claims may serve as a summary of the disclosure.

BRIEF DESCRIPTION OF THE DRAWINGS

In the drawings:

FIG. 2 illustrates two views of an example logical organization of sets of instructions in main memory when an example mobile application is loaded for execution.

FIG. 5 depicts an example embodiment of a timeline view for data entry.

FIG. 6 depicts an example embodiment of a spreadsheet view for data entry.

DETAILED DESCRIPTION

In the following description, for the purposes of explanation, numerous specific details are set forth in order to provide a thorough understanding of the present disclosure. It will be apparent, however, that embodiments may be practiced without these specific details. In other instances, well-known structures and devices are shown in block diagram form in order to avoid unnecessarily obscuring the present disclosure. Embodiments are disclosed in sections according to the following outline:

1. GENERAL OVERVIEW
2. EXAMPLE AGRICULTURAL INTELLIGENCE COMPUTER SYSTEM
   2.1. STRUCTURAL OVERVIEW
   2.2. APPLICATION PROGRAM OVERVIEW
   2.3. DATA INGEST TO THE COMPUTER SYSTEM
   2.4. PROCESS OVERVIEW—AGRONOMIC MODEL TRAINING
   2.5. IMPLEMENTATION EXAMPLE—HARDWARE OVERVIEW
3. SOIL TESTING SYSTEM

1. General Overview

Aspects of the disclosure generally relate to techniques and devices for testing the quality of a soil sample. In an embodiment, a soil probe is positioned above a region of a field. Force is applied to the soil prove such, causing the soil probe to obtain a sample of the soil extending into the soil. A soil sample quality criterion is determined based on the soil sample and is associated with the soil sample.

In an embodiment, a method comprises: positioning a soil probe above a region of a field; applying a force to the soil probe such that the soil probe obtains a soil sample, the soil sample extending a first depth into the soil; determining a soil sample quality criterion; and associating the soil sample with the soil sample quality criterion. In an embodiment, a soil testing system comprises: a soil probe having a hollow portion for receiving a soil sample; a soil sample quality measurement device; and a computer system in data communication with the soil sample quality measurement device, the computer system configured to associate the soil sample with the soil sample quality criterion.

2. Example Agricultural Intelligence Computer System 2.1 Structural Overview

Figure 1:
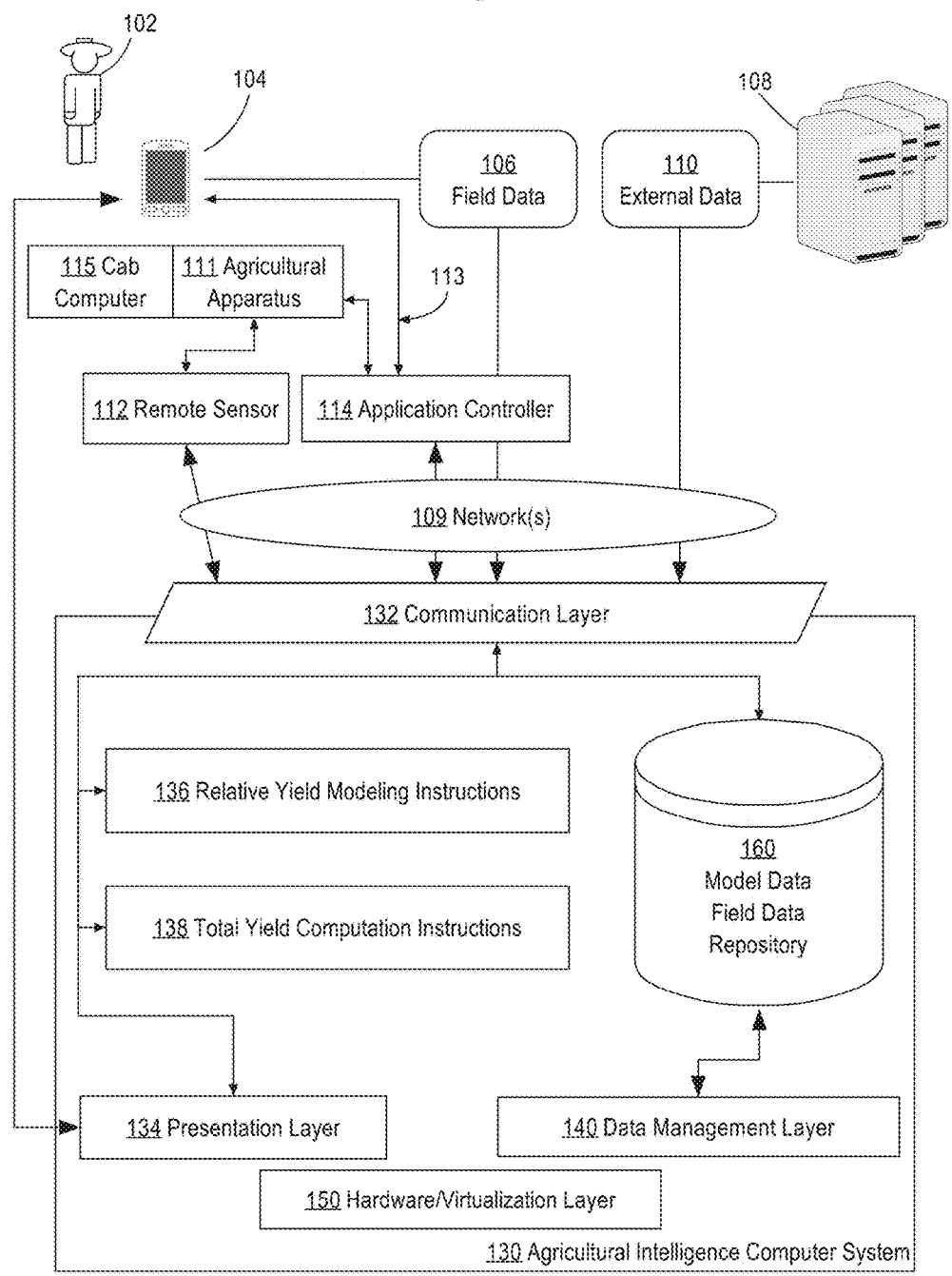
FIG. 1 illustrates an example computer system that is configured to perform the functions described herein, shown in a field environment with other apparatus with which the system may interoperate.

FIG. 1 illustrates an example computer system that is configured to perform the functions described herein, shown in a field environment with other apparatus with which the system may interoperate. In one embodiment, a user 102 owns, operates or possesses a field manager computing device 104 in a field location or associated with a field location such as a field intended for agricultural activities or a management location for one or more agricultural fields. The field manager computer device 104 is programmed or configured to provide field data 106 to an agricultural intelligence computer system 130 via one or more networks 109.

Examples of field data 106 include (a) identification data (for example, acreage, field name, field identifiers, geographic identifiers, boundary identifiers, crop identifiers, and any other suitable data that may be used to identify farm land, such as a common land unit (CLU), lot and block number, a parcel number, geographic coordinates and boundaries, Farm Serial Number (FSN), farm number, tract number, field number, section, township, and/or range), (b) harvest data (for example, crop type, crop variety, crop rotation, whether the crop is grown organically, harvest date, Actual Production History (APH), expected yield, yield, crop price, crop revenue, grain moisture, tillage practice, and previous growing season information), (c) soil data (for example, type, composition, pH, organic matter (OM), cation exchange capacity (CEC)), (d) planting data (for example, planting date, seed(s) type, relative maturity (RM) of planted seed(s), seed population), (e) fertilizer data (for example, nutrient type (Nitrogen, Phosphorous, Potassium), application type, application date, amount, source, method), (f) pesticide data (for example, pesticide, herbicide, fungicide, other substance or mixture of substances intended for use as a plant regulator, defoliant, or desiccant, application date, amount, source, method), (g) irrigation data (for example, application date, amount, source, method), (h) weather data (for example, precipitation, temperature, wind, forecast, pressure, visibility, clouds, heat index, dew point, humidity, snow depth, air quality, sunrise, sunset), (i) imagery data (for example, imagery and light spectrum information from an agricultural apparatus sensor, camera, computer, smartphone, tablet, unmanned aerial vehicle, planes or satellite), (j) scouting observations (photos, videos, free form notes, voice recordings, voice transcriptions, weather conditions (temperature, precipitation (current and over time), soil moisture, crop growth stage, wind velocity, relative humidity, dew point, black layer)), and (k) soil, seed, crop phenology, pest and disease reporting, and predictions sources and databases.

A data server computer 108 is communicatively coupled to agricultural intelligence computer system 130 and is programmed or configured to send external data 110 to agricultural intelligence computer system 130 via the network(s) 109. The external data server computer 108 may be owned or operated by the same legal person or entity as the agricultural intelligence computer system 130, or by a different person or entity such as a government agency, non-governmental organization (NGO), and/or a private data service provider. Examples of external data include weather data, imagery data, soil data, or statistical data relating to crop yields, among others. External data 110 may consist of the same type of information as field data 106. In some embodiments, the external data 110 is provided by an external data server 108 owned by the same entity that owns and/or operates the agricultural intelligence computer system 130. For example, the agricultural intelligence computer system 130 may include a data server focused exclusively on a type of data that might otherwise be obtained from third party sources, such as weather data. In some embodiments, an external data server 108 may actually be incorporated within the system 130.

An agricultural apparatus 111 has one or more remote sensors 112 fixed thereon, which sensors are communicatively coupled either directly or indirectly via agricultural apparatus 111 to the agricultural intelligence computer system 130 and are programmed or configured to send sensor data to agricultural intelligence computer system 130. Examples of agricultural apparatus 111 include tractors, combines, harvesters, planters, trucks, fertilizer equipment, unmanned aerial vehicles, and any other item of physical machinery or hardware, typically mobile machinery, and which may be used in tasks associated with agriculture. In some embodiments, a single unit of apparatus 111 may comprise a plurality of sensors 112 that are coupled locally in a network on the apparatus; controller area network (CAN) is example of such a network that can be installed in combines or harvesters. Application controller 114 is communicatively coupled to agricultural intelligence computer system 130 via the network(s) 109 and is programmed or configured to receive one or more scripts to control an operating parameter of an agricultural vehicle or implement from the agricultural intelligence computer system 130. For instance, a controller area network (CAN) bus interface may be used to enable communications from the agricultural intelligence computer system 130 to the agricultural apparatus 111, such as how the CLIMATE FIELDVIEW DRIVE, available from The Climate Corporation, San Francisco, Calif., is used. Sensor data may consist of the same type of information as field data 106.

The apparatus 111 may comprise a cab computer 115 that is programmed with a cab application, which may comprise a version or variant of the mobile application for device 104 that is further described in other sections herein. In an embodiment, cab computer 115 comprises a compact computer, often a tablet-sized computer or smartphone, with a color graphical screen display that is mounted within an operator's cab of the apparatus 111. Cab computer 115 may implement some or all of the operations and functions that are described further herein for the mobile computer device 104.

The network(s) 109 broadly represent any combination of one or more data communication networks including local area networks, wide area networks, internetworks or internets, using any of wireline or wireless links, including terrestrial or satellite links. The network(s) may be implemented by any medium or mechanism that provides for the exchange of data between the various elements of FIG. 1. The various elements of FIG. 1 may also have direct (wired or wireless) communications links. The sensors 112, controller 114, external data server computer 108, and other elements of the system each comprise an interface compatible with the network(s) 109 and are programmed or configured to use standardized protocols for communication across the networks such as TCP/IP, Bluetooth, CAN protocol and higher-layer protocols such as HTTP, TLS, and the like.

Agricultural intelligence computer system 130 is programmed or configured to receive field data 106 from field manager computing device 104, external data 110 from external data server computer 108, and sensor data from remote sensor 112. Agricultural intelligence computer system 130 may be further configured to host, use or execute one or more computer programs, other software elements, digitally programmed logic such as FPGAs or ASICs, or any combination thereof to perform translation and storage of data values, construction of digital models of one or more crops on one or more fields, generation of recommendations and notifications, and generation and sending of scripts to application controller 114, in the manner described further in other sections of this disclosure.

In an embodiment, agricultural intelligence computer system 130 is programmed with or comprises a communication layer 132, presentation layer 134, data management layer 140, hardware/virtualization layer 150, and model and field data repository 160. "Layer," in this context, refers to any combination of electronic digital interface circuits, microcontrollers, firmware such as drivers, and/or computer programs or other software elements.

Communication layer 132 may be programmed or configured to perform input/output interfacing functions including sending requests to field manager computing device 104, external data server computer 108, and remote sensor 112 for field data, external data, and sensor data respectively. Communication layer 132 may be programmed or configured to send the received data to model and field data repository 160 to be stored as field data 106.

Presentation layer 134 may be programmed or configured to generate a graphical user interface (GUI) to be displayed on field manager computing device 104, cab computer 115 or other computers that are coupled to the system 130 through the network 109. The GUI may comprise controls for inputting data to be sent to agricultural intelligence computer system 130, generating requests for models and/or recommendations, and/or displaying recommendations, notifications, models, and other field data.

Data management layer 140 may be programmed or configured to manage read operations and write operations involving the repository 160 and other functional elements of the system, including queries and result sets communicated between the functional elements of the system and the repository. Examples of data management layer 140 include JDBC, SQL server interface code, and/or HADOOP interface code, among others. Repository 160 may comprise a database. As used herein, the term "database" may refer to either a body of data, a relational database management system (RDBMS), or to both. As used herein, a database may comprise any collection of data including hierarchical databases, relational databases, flat file databases, object-relational databases, object oriented databases, and any other structured collection of records or data that is stored in a computer system. Examples of RDBMS's include, but are not limited to including, ORACLE®, MYSQL, IBM® DB2, MICROSOFT® SQL SERVER, SYBASE®, and POSTGR-ESQL databases. However, any database may be used that enables the systems and methods described herein.

When field data 106 is not provided directly to the agricultural intelligence computer system via one or more agricultural machines or agricultural machine devices that interacts with the agricultural intelligence computer system, the user may be prompted via one or more user interfaces on the user device (served by the agricultural intelligence computer system) to input such information. In an example embodiment, the user may specify identification data by accessing a map on the user device (served by the agricultural intelligence computer system) and selecting specific CLUs that have been graphically shown on the map. In an alternative embodiment, the user 102 may specify identification data by accessing a map on the user device (served by the agricultural intelligence computer system 130) and drawing boundaries of the field over the map. Such CLU selection or map drawings represent geographic identifiers. In alternative embodiments, the user may specify identification data by accessing field identification data (provided as shape files or in a similar format) from the U. S. Department of Agriculture Farm Service Agency or other source via the user device and providing such field identification data to the agricultural intelligence computer system.

In an example embodiment, the agricultural intelligence computer system 130 is programmed to generate and cause displaying a graphical user interface comprising a data manager for data input. After one or more fields have been identified using the methods described above, the data manager may provide one or more graphical user interface widgets which when selected can identify changes to the field, soil, crops, tillage, or nutrient practices. The data manager may include a timeline view, a spreadsheet view, and/or one or more editable programs.

Figure 5:
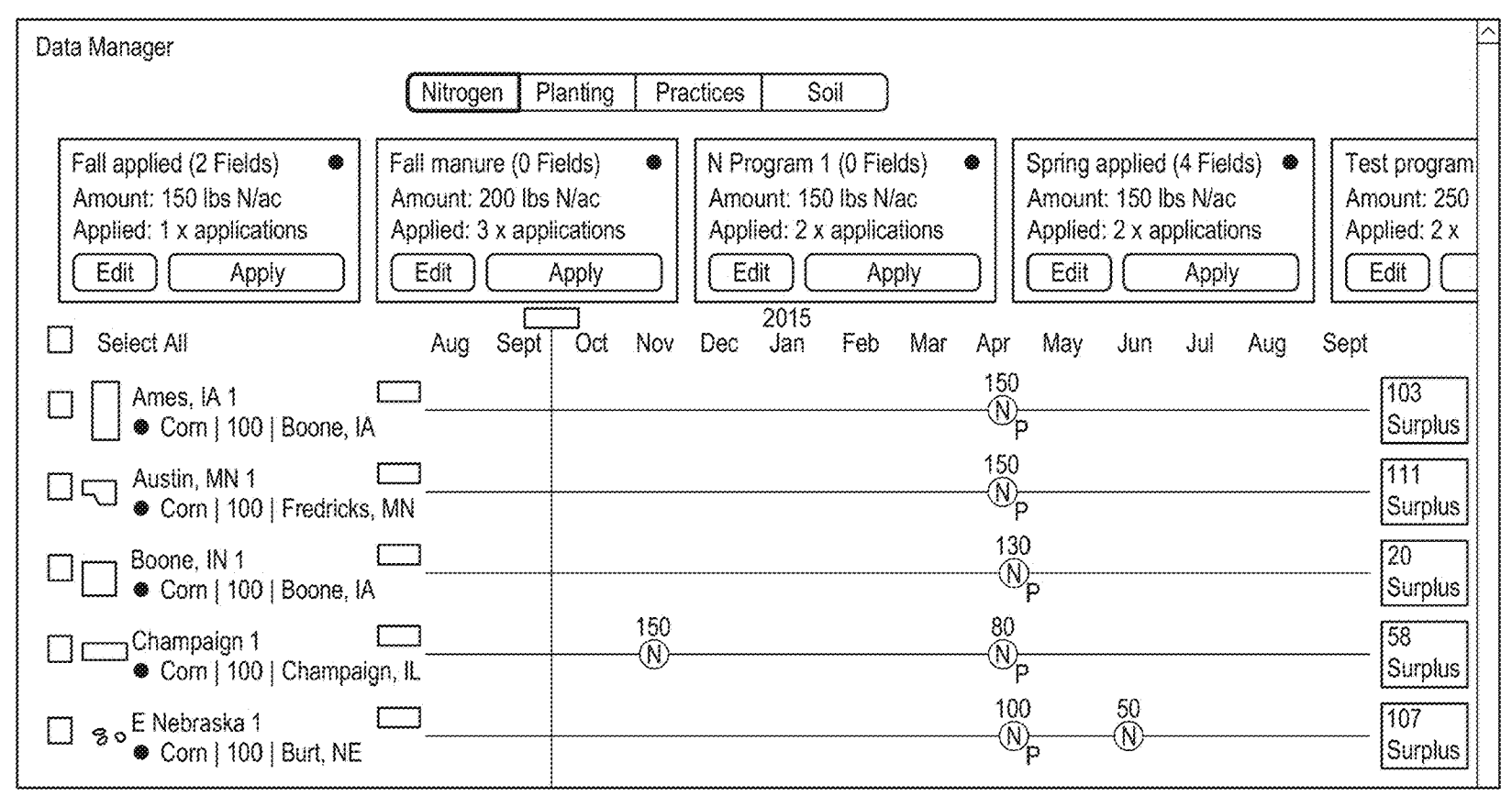

FIG. 5 depicts an example embodiment of a timeline view for data entry. Using the display depicted in FIG. 5, a user computer can input a selection of a particular field and a particular date for the addition of event. Events depicted at the top of the timeline include Nitrogen, Planting, Practices, and Soil. To add a nitrogen application event, a user computer may provide input to select the nitrogen tab. The user computer may then select a location on the timeline for a particular field in order to indicate an application of nitrogen on the selected field. In response to receiving a selection of a location on the timeline for a particular field, the data manager may display a data entry overlay, allowing the user computer to input data pertaining to nitrogen applications, planting procedures, soil application, tillage procedures, irrigation practices, or other information relating to the particular field. For example, if a user computer selects a portion of the timeline and indicates an application of nitrogen, then the data entry overlay may include fields for inputting an amount of nitrogen applied, a date of application, a type of fertilizer used, and any other information related to the application of nitrogen.

In an embodiment, the data manager provides an interface for creating one or more programs. "Program," in this context, refers to a set of data pertaining to nitrogen applications, planting procedures, soil application, tillage procedures, irrigation practices, or other information that may be related to one or more fields, and that can be stored in digital data storage for reuse as a set in other operations. After a program has been created, it may be conceptually applied to one or more fields and references to the program may be stored in digital storage in association with data identifying the fields. Thus, instead of manually entering identical data relating to the same nitrogen applications for multiple different fields, a user computer may create a program that indicates a particular application of nitrogen and then apply the program to multiple different fields. For example, in the timeline view of FIG. 5, the top two timelines have the "Fall applied" program selected, which includes an application of 150 lbs N/ac in early April. The data manager may provide an interface for editing a program. In an embodiment, when a particular program is edited, each field that has selected the particular program is edited. For example, in FIG. 5, if the "Fall applied" program is edited to reduce the application of nitrogen to 130 lbs N/ac, the top two fields may be updated with a reduced application of nitrogen based on the edited program.

In an embodiment, in response to receiving edits to a field that has a program selected, the data manager removes the correspondence of the field to the selected program. For example, if a nitrogen application is added to the top field in FIG. 5, the interface may update to indicate that the "Fall applied" program is no longer being applied to the top field. While the nitrogen application in early April may remain, updates to the "Fall applied" program would not alter the April application of nitrogen.

FIG. 6 depicts an example embodiment of a spreadsheet view for data entry. Using the display depicted in FIG. 6, a user can create and edit information for one or more fields. The data manager may include spreadsheets for inputting information with respect to Nitrogen, Planting, Practices, and Soil as depicted in FIG. 6. To edit a particular entry, a user computer may select the particular entry in the spreadsheet and update the values. For example, FIG. 6 depicts an in-progress update to a target yield value for the second field. Additionally, a user computer may select one or more fields in order to apply one or more programs. In response to receiving a selection of a program for a particular field, the data manager may automatically complete the entries for the particular field based on the selected program. As with the timeline view, the data manager may update the entries for each field associated with a particular program in response to receiving an update to the program. Additionally, the data manager may remove the correspondence of the selected program to the field in response to receiving an edit to one of the entries for the field.

In an embodiment, model and field data is stored in model and field data repository 160. Model comprises data models created for one or more fields. For example, a crop model may include a digitally constructed model of the development of a crop on the one or more fields. "Model," in this context, refers to an electronic digitally stored set of executable instructions and data values, associated with one another, which are capable of receiving and responding to a programmatic or other digital call, invocation, or request for resolution based upon specified input values, to yield one or more stored output values that can serve as the basis of computer-implemented recommendations, output data displays, or machine control, among other things. Persons of skill in the field find it convenient to express models using mathematical equations, but that form of expression does not confine the models disclosed herein to abstract concepts; instead, each model herein has a practical application in a computer in the form of stored executable instructions and data that implement the model using the computer. The model may include a model of past events on the one or more fields, a model of the current status of the one or more fields, and/or a model of predicted events on the one or more fields. Model and field data may be stored in data structures in memory, rows in a database table, in flat files or spreadsheets, or other forms of stored digital data.

Figure 4:
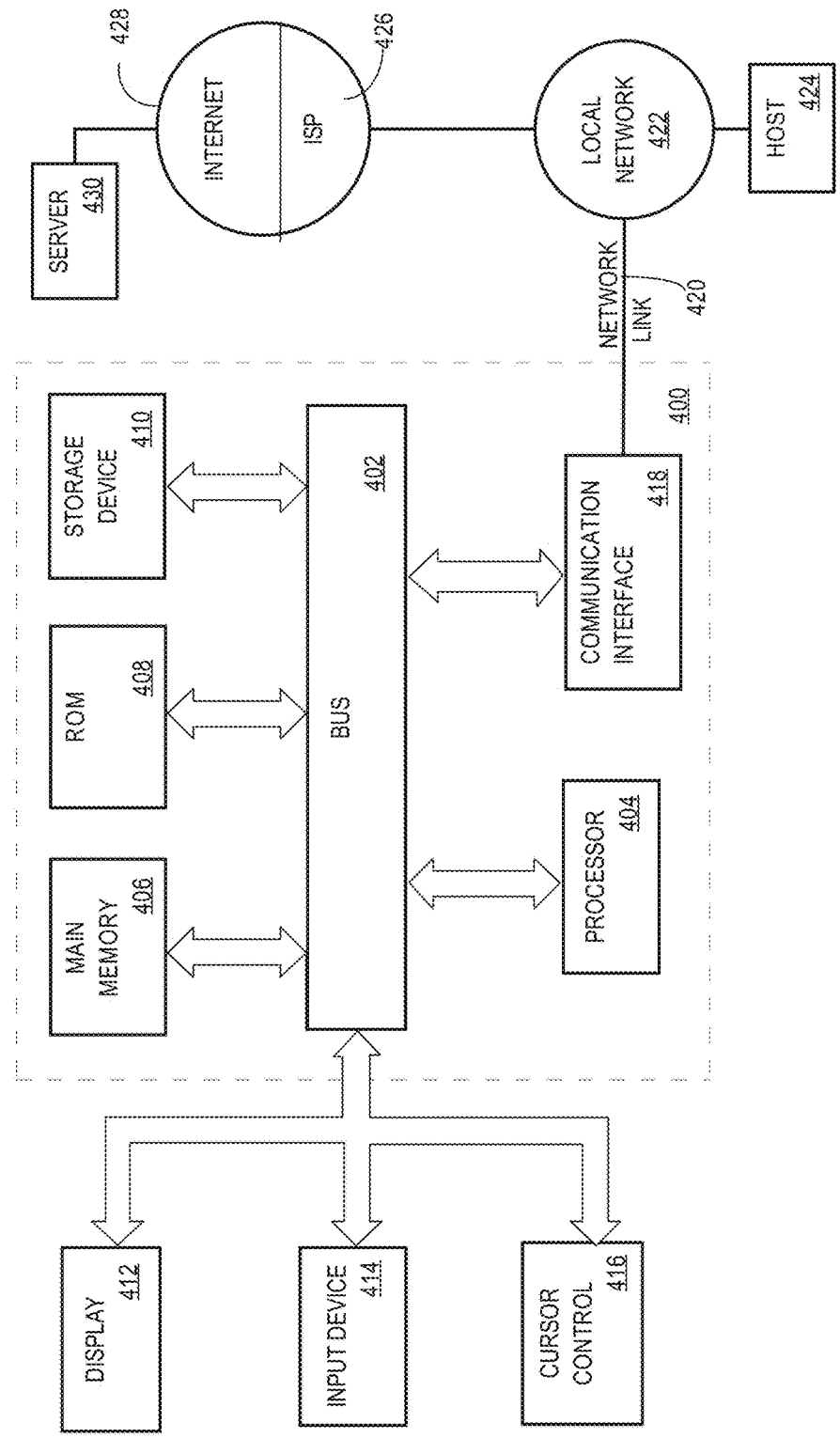
FIG. 4 is a block diagram that illustrates a computer system 400 upon which an embodiment of the invention may be implemented.

Hardware/virtualization layer 150 comprises one or more central processing units (CPUs), memory controllers, and other devices, components, or elements of a computer system such as volatile or non-volatile memory, non-volatile storage such as disk, and I/O devices or interfaces as illustrated and described, for example, in connection with FIG. 4. The layer 150 also may comprise programmed instructions that are configured to support virtualization, containerization, or other technologies.

For purposes of illustrating a clear example, FIG. 1 shows a limited number of instances of certain functional elements. However, in other embodiments, there may be any number of such elements. For example, embodiments may use thousands or millions of different mobile computing devices 104 associated with different users. Further, the system 130 and/or external data server computer 108 may be implemented using two or more processors, cores, clusters, or instances of physical machines or virtual machines, configured in a discrete location or co-located with other elements in a datacenter, shared computing facility or cloud computing facility.

2.2. Application Program Overview

In an embodiment, the implementation of the functions described herein using one or more computer programs or other software elements that are loaded into and executed using one or more general-purpose computers will cause the general-purpose computers to be configured as a particular machine or as a computer that is specially adapted to perform the functions described herein. Further, each of the flow diagrams that are described further herein may serve, alone or in combination with the descriptions of processes and functions in prose herein, as algorithms, plans or directions that may be used to program a computer or logic to implement the functions that are described. In other words, all the prose text herein, and all the drawing figures, together are intended to provide disclosure of algorithms, plans or directions that are sufficient to permit a skilled person to program a computer to perform the functions that are described herein, in combination with the skill and knowledge of such a person given the level of skill that is appropriate for inventions and disclosures of this type.

In an embodiment, user 102 interacts with agricultural intelligence computer system 130 using field manager computing device 104 configured with an operating system and one or more application programs or apps; the field manager computing device 104 also may interoperate with the agricultural intelligence computer system independently and automatically under program control or logical control and direct user interaction is not always required. Field manager computing device 104 broadly represents one or more of a smart phone, PDA, tablet computing device, laptop computer, desktop computer, workstation, or any other computing device capable of transmitting and receiving information and performing the functions described herein. Field manager computing device 104 may communicate via a network using a mobile application stored on field manager computing device 104, and in some embodiments, the device may be coupled using a cable 113 or connector to the sensor 112 and/or controller 114. A particular user 102 may own, operate or possess and use, in connection with system 130, more than one field manager computing device 104 at a time.

The mobile application may provide client-side functionality, via the network to one or more mobile computing devices. In an example embodiment, field manager computing device 104 may access the mobile application via a web browser or a local client application or app. Field manager computing device 104 may transmit data to, and receive data from, one or more front-end servers, using web-based protocols or formats such as HTTP, XML, and/or JSON, or app-specific protocols. In an example embodiment, the data may take the form of requests and user information input, such as field data, into the mobile computing device. In some embodiments, the mobile application interacts with location tracking hardware and software on field manager computing device 104 which determines the location of field manager computing device 104 using standard tracking techniques such as multilateration of radio signals, the global positioning system (GPS), WiFi positioning systems, or other methods of mobile positioning. In some cases, location data or other data associated with the device 104, user 102, and/or user account(s) may be obtained by queries to an operating system of the device or by requesting an app on the device to obtain data from the operating system.

In an embodiment, field manager computing device 104 sends field data 106 to agricultural intelligence computer system 130 comprising or including, but not limited to, data values representing one or more of: a geographical location of the one or more fields, tillage information for the one or more fields, crops planted in the one or more fields, and soil data extracted from the one or more fields. Field manager computing device 104 may send field data 106 in response to user input from user 102 specifying the data values for the one or more fields. Additionally, field manager computing device 104 may automatically send field data 106 when one or more of the data values becomes available to field manager computing device 104. For example, field manager computing device 104 may be communicatively coupled to remote sensor 112 and/or application controller 114. In response to receiving data indicating that application controller 114 released water onto the one or more fields, field manager computing device 104 may send field data 106 to agricultural intelligence computer system 130 indicating that water was released on the one or more fields. Field data 106 identified in this disclosure may be input and communicated using electronic digital data that is communicated between computing devices using parameterized URLs over HTTP, or another suitable communication or messaging protocol.

A commercial example of the mobile application is CLIMATE FIELDVIEW, commercially available from The Climate Corporation, San Francisco, Calif. The CLIMATE FIELDVIEW application, or other applications, may be modified, extended, or adapted to include features, functions, and programming that have not been disclosed earlier than the filing date of this disclosure. In one embodiment, the mobile application comprises an integrated software platform that allows a grower to make fact-based decisions for their operation because it combines historical data about the grower's fields with any other data that the grower wishes to compare. The combinations and comparisons may be performed in real time and are based upon scientific models that provide potential scenarios to permit the grower to make better, more informed decisions.

FIG. 2 illustrates two views of an example logical organization of sets of instructions in main memory when an example mobile application is loaded for execution. In FIG. 2, each named element represents a region of one or more pages of RAM or other main memory, or one or more blocks of disk storage or other non-volatile storage, and the programmed instructions within those regions. In one embodiment, in view (a), a mobile computer application 200 comprises account-fields-data ingestion-sharing instructions 202, overview and alert instructions 204, digital map book instructions 206, seeds and planting instructions 208, nitrogen instructions 210, weather instructions 212, field health instructions 214, and performance instructions 216.

In one embodiment, a mobile computer application 200 comprises account-fields-data ingestion-sharing instructions 202 which are programmed to receive, translate, and ingest field data from third party systems via manual upload or APIs. Data types may include field boundaries, yield maps, as-planted maps, soil test results, as-applied maps, and/or management zones, among others. Data formats may include shape files, native data formats of third parties, and/or farm management information system (FMIS) exports, among others. Receiving data may occur via manual upload, e-mail with attachment, external APIs that push data to the mobile application, or instructions that call APIs of external systems to pull data into the mobile application. In one embodiment, mobile computer application 200 comprises a data inbox. In response to receiving a selection of the data inbox, the mobile computer application 200 may display a graphical user interface for manually uploading data files and importing uploaded files to a data manager.

In one embodiment, digital map book instructions 206 comprise field map data layers stored in device memory and are programmed with data visualization tools and geospatial field notes. This provides growers with convenient information close at hand for reference, logging and visual insights into field performance. In one embodiment, overview and alert instructions 204 are programmed to provide an operation-wide view of what is important to the grower, and timely recommendations to take action or focus on particular issues. This permits the grower to focus time on what needs attention, to save time and preserve yield throughout the season. In one embodiment, seeds and planting instructions 208 are programmed to provide tools for seed selection, hybrid placement, and script creation, including variable rate (VR) script creation, based upon scientific models and empirical data. This enables growers to maximize yield or return on investment through optimized seed purchase, placement and population.

In one embodiment, script generation instructions 205 are programmed to provide an interface for generating scripts, including variable rate (VR) fertility scripts. The interface enables growers to create scripts for field implements, such as nutrient applications, planting, and irrigation. For example, a planting script interface may comprise tools for identifying a type of seed for planting. Upon receiving a selection of the seed type, mobile computer application 200 may display one or more fields broken into management zones, such as the field map data layers created as part of digital map book instructions 206. In one embodiment, the management zones comprise soil zones along with a panel identifying each soil zone and a soil name, texture, drainage for each zone, or other field data. Mobile computer application 200 may also display tools for editing or creating such, such as graphical tools for drawing management zones, such as soil zones, over a map of one or more fields. Planting procedures may be applied to all management zones or different planting procedures may be applied to different subsets of management zones. When a script is created, mobile computer application 200 may make the script available for download in a format readable by an application controller, such as an archived or compressed format. Additionally and/or alternatively, a script may be sent directly to cab computer 115 from mobile computer application 200 and/or uploaded to one or more data servers and stored for further use.

In one embodiment, nitrogen instructions 210 are programmed to provide tools to inform nitrogen decisions by visualizing the availability of nitrogen to crops. This enables growers to maximize yield or return on investment through optimized nitrogen application during the season. Example programmed functions include displaying images such as SSURGO images to enable drawing of application zones and/or images generated from subfield soil data, such as data obtained from sensors, at a high spatial resolution (as fine as 10 meters or smaller because of their proximity to the soil); upload of existing grower-defined zones; providing an application graph and/or a map to enable tuning application(s) of nitrogen across multiple zones; output of scripts to drive machinery; tools for mass data entry and adjustment; and/or maps for data visualization, among others. "Mass data entry," in this context, may mean entering data once and then applying the same data to multiple fields that have been defined in the system; example data may include nitrogen application data that is the same for many fields of the same grower, but such mass data entry applies to the entry of any type of field data into the mobile computer application 200. For example, nitrogen instructions 210 may be programmed to accept definitions of nitrogen planting and practices programs and to accept user input specifying to apply those programs across multiple fields. "Nitrogen planting programs," in this context, refers to a stored, named set of data that associates: a name, color code or other identifier, one or more dates of application, types of material or product for each of the dates and amounts, method of application or incorporation such as injected or knifed in, and/or amounts or rates of application for each of the dates, crop or hybrid that is the subject of the application, among others. "Nitrogen practices programs," in this context, refers to a stored, named set of data that associates: a practices name; a previous crop; a tillage system; a date of primarily tillage; one or more previous tillage systems that were used; one or more indicators of application type, such as manure, that were used. Nitrogen instructions 210 also may be programmed to generate and cause displaying a nitrogen graph, which indicates projections of plant use of the specified nitrogen and whether a surplus or shortfall is predicted; in some embodiments, different color indicators may signal a magnitude of surplus or magnitude of shortfall. In one embodiment, a nitrogen graph comprises a graphical display in a computer display device comprising a plurality of rows, each row associated with and identifying a field; data specifying what crop is planted in the field, the field size, the field location, and a graphic representation of the field perimeter; in each row, a timeline by month with graphic indicators specifying each nitrogen application and amount at points correlated to month names; and numeric and/or colored indicators of surplus or shortfall, in which color indicates magnitude.

In one embodiment, the nitrogen graph may include one or more user input features, such as dials or slider bars, to dynamically change the nitrogen planting and practices programs so that a user may optimize his nitrogen graph. The user may then use his optimized nitrogen graph and the related nitrogen planting and practices programs to implement one or more scripts, including variable rate (VR) fertility scripts. Nitrogen instructions 210 also may be programmed to generate and cause displaying a nitrogen map, which indicates projections of plant use of the specified nitrogen and whether a surplus or shortfall is predicted; in some embodiments, different color indicators may signal a magnitude of surplus or magnitude of shortfall. The nitrogen map may display projections of plant use of the specified nitrogen and whether a surplus or shortfall is predicted for different times in the past and the future (such as daily, weekly, monthly or yearly) using numeric and/or colored indicators of surplus or shortfall, in which color indicates magnitude. In one embodiment, the nitrogen map may include one or more user input features, such as dials or slider bars, to dynamically change the nitrogen planting and practices programs so that a user may optimize his nitrogen map, such as to obtain a preferred amount of surplus to shortfall. The user may then use his optimized nitrogen map and the related nitrogen planting and practices programs to implement one or more scripts, including variable rate (VR) fertility scripts. In other embodiments, similar instructions to the nitrogen instructions 210 could be used for application of other nutrients (such as phosphorus and potassium) application of pesticide, and irrigation programs.

In one embodiment, weather instructions 212 are programmed to provide field-specific recent weather data and forecasted weather information. This enables growers to save time and have an efficient integrated display with respect to daily operational decisions.

In one embodiment, field health instructions 214 are programmed to provide timely remote sensing images highlighting in-season crop variation and potential concerns. Example programmed functions include cloud checking, to identify possible clouds or cloud shadows; determining nitrogen indices based on field images; graphical visualization of scouting layers, including, for example, those related to field health, and viewing and/or sharing of scouting notes; and/or downloading satellite images from multiple sources and prioritizing the images for the grower, among others.

In one embodiment, performance instructions 216 are programmed to provide reports, analysis, and insight tools using on-farm data for evaluation, insights and decisions. This enables the grower to seek improved outcomes for the next year through fact-based conclusions about why return on investment was at prior levels, and insight into yield-limiting factors. The performance instructions 216 may be programmed to communicate via the network(s) 109 to back-end analytics programs executed at agricultural intelligence computer system 130 and/or external data server computer 108 and configured to analyze metrics such as yield, hybrid, population, SSURGO, soil tests, or elevation, among others. Programmed reports and analysis may include yield variability analysis, benchmarking of yield and other metrics against other growers based on anonymized data collected from many growers, or data for seeds and planting, among others.

Applications having instructions configured in this way may be implemented for different computing device platforms while retaining the same general user interface appearance. For example, the mobile application may be programmed for execution on tablets, smartphones, or server computers that are accessed using browsers at client computers. Further, the mobile application as configured for tablet computers or smartphones may provide a full app experience or a cab app experience that is suitable for the display and processing capabilities of cab computer 115. For example, referring now to view (b) of FIG. 2, in one embodiment a cab computer application 220 may comprise maps-cab instructions 222, remote view instructions 224, data collect and transfer instructions 226, machine alerts instructions 228, script transfer instructions 230, and scouting-cab instructions 232. The code base for the instructions of view (b) may be the same as for view (a) and executables implementing the code may be programmed to detect the type of platform on which they are executing and to expose, through a graphical user interface, only those functions that are appropriate to a cab platform or full platform. This approach enables the system to recognize the distinctly different user experience that is appropriate for an in-cab environment and the different technology environment of the cab. The maps-cab instructions 222 may be programmed to provide map views of fields, farms or regions that are useful in directing machine operation. The remote view instructions 224 may be programmed to turn on, manage, and provide views of machine activity in real-time or near real-time to other computing devices connected to the system 130 via wireless networks, wired connectors or adapters, and the like. The data collect and transfer instructions 226 may be programmed to turn on, manage, and provide transfer of data collected at machine sensors and controllers to the system 130 via wireless networks, wired connectors or adapters, and the like. The machine alerts instructions 228 may be programmed to detect issues with operations of the machine or tools that are associated with the cab and generate operator alerts. The script transfer instructions 230 may be configured to transfer in scripts of instructions that are configured to direct machine operations or the collection of data. The scouting-cab instructions 230 may be programmed to display location-based alerts and information received from the system 130 based on the location of the agricultural apparatus 111 or sensors 112 in the field and ingest, manage, and provide transfer of location-based scouting observations to the system 130 based on the location of the agricultural apparatus 111 or sensors 112 in the field.

2.3. Data Ingest to the Computer System

In an embodiment, external data server computer 108 stores external data 110, including soil data representing soil composition for the one or more fields and weather data representing temperature and precipitation on the one or more fields. The weather data may include past and present weather data as well as forecasts for future weather data. In an embodiment, external data server computer 108 comprises a plurality of servers hosted by different entities. For example, a first server may contain soil composition data while a second server may include weather data. Additionally, soil composition data may be stored in multiple servers. For example, one server may store data representing percentage of sand, silt, and clay in the soil while a second server may store data representing percentage of organic matter (OM) in the soil.

In an embodiment, remote sensor 112 comprises one or more sensors that are programmed or configured to produce one or more observations. Remote sensor 112 may be aerial sensors, such as satellites, vehicle sensors, planting equipment sensors, tillage sensors, fertilizer or insecticide application sensors, harvester sensors, and any other implement capable of receiving data from the one or more fields. In an embodiment, application controller 114 is programmed or configured to receive instructions from agricultural intelligence computer system 130. Application controller 114 may also be programmed or configured to control an operating parameter of an agricultural vehicle or implement. For example, an application controller may be programmed or configured to control an operating parameter of a vehicle, such as a tractor, planting equipment, tillage equipment, fertilizer or insecticide equipment, harvester equipment, or other farm implements such as a water valve. Other embodiments may use any combination of sensors and controllers, of which the following are merely selected examples.

The system 130 may obtain or ingest data under user 102 control, on a mass basis from a large number of growers who have contributed data to a shared database system. This form of obtaining data may be termed "manual data ingest" as one or more user-controlled computer operations are requested or triggered to obtain data for use by the system 130. As an example, the CLIMATE FIELDVIEW application, commercially available from The Climate Corporation, San Francisco, Calif., may be operated to export data to system 130 for storing in the repository 160.

For example, seed monitor systems can both control planter apparatus components and obtain planting data, including signals from seed sensors via a signal harness that comprises a CAN backbone and point-to-point connections for registration and/or diagnostics. Seed monitor systems can be programmed or configured to display seed spacing, population and other information to the user via the cab computer 115 or other devices within the system 130. Examples are disclosed in U.S. Pat. No. 8,738,243 and US Pat. Pub. 20150094916, and the present disclosure assumes knowledge of those other patent disclosures.

Likewise, yield monitor systems may contain yield sensors for harvester apparatus that send yield measurement data to the cab computer 115 or other devices within the system 130. Yield monitor systems may utilize one or more remote sensors 112 to obtain grain moisture measurements in a combine or other harvester and transmit these measurements to the user via the cab computer 115 or other devices within the system 130.

In an embodiment, examples of sensors 112 that may be used with any moving vehicle or apparatus of the type described elsewhere herein include kinematic sensors and position sensors. Kinematic sensors may comprise any of speed sensors such as radar or wheel speed sensors, accelerometers, or gyros. Position sensors may comprise GPS receivers or transceivers, or WiFi-based position or mapping apps that are programmed to determine location based upon nearby WiFi hotspots, among others.

In an embodiment, examples of sensors 112 that may be used with tractors or other moving vehicles include engine speed sensors, fuel consumption sensors, area counters or distance counters that interact with GPS or radar signals, PTO (power take-off) speed sensors, tractor hydraulics sensors configured to detect hydraulics parameters such as pressure or flow, and/or and hydraulic pump speed, wheel speed sensors or wheel slippage sensors. In an embodiment, examples of controllers 114 that may be used with tractors include hydraulic directional controllers, pressure controllers, and/or flow controllers; hydraulic pump speed controllers; speed controllers or governors; hitch position controllers; or wheel position controllers provide automatic steering.

In an embodiment, examples of sensors 112 that may be used with seed planting equipment such as planters, drills, or air seeders include seed sensors, which may be optical, electromagnetic, or impact sensors; downforce sensors such as load pins, load cells, pressure sensors; soil property sensors such as reflectivity sensors, moisture sensors, electrical conductivity sensors, optical residue sensors, or temperature sensors; component operating criteria sensors such as planting depth sensors, downforce cylinder pressure sensors, seed disc speed sensors, seed drive motor encoders, seed conveyor system speed sensors, or vacuum level sensors; or pesticide application sensors such as optical or other electromagnetic sensors, or impact sensors. In an embodiment, examples of controllers 114 that may be used with such seed planting equipment include: toolbar fold controllers, such as controllers for valves associated with hydraulic cylinders; downforce controllers, such as controllers for valves associated with pneumatic cylinders, airbags, or hydraulic cylinders, and programmed for applying downforce to individual row units or an entire planter frame; planting depth controllers, such as linear actuators; metering controllers, such as electric seed meter drive motors, hydraulic seed meter drive motors, or swath control clutches; hybrid selection controllers, such as seed meter drive motors, or other actuators programmed for selectively allowing or preventing seed or an air-seed mixture from delivering seed to or from seed meters or central bulk hoppers; metering controllers, such as electric seed meter drive motors, or hydraulic seed meter drive motors; seed conveyor system controllers, such as controllers for a belt seed delivery conveyor motor; marker controllers, such as a controller for a pneumatic or hydraulic actuator; or pesticide application rate controllers, such as metering drive controllers, orifice size or position controllers.

In an embodiment, examples of sensors 112 that may be used with tillage equipment include position sensors for tools such as shanks or discs; tool position sensors for such tools that are configured to detect depth, gang angle, or lateral spacing; downforce sensors; or draft force sensors. In an embodiment, examples of controllers 114 that may be used with tillage equipment include downforce controllers or tool position controllers, such as controllers configured to control tool depth, gang angle, or lateral spacing.

In an embodiment, examples of sensors 112 that may be used in relation to apparatus for applying fertilizer, insecticide, fungicide and the like, such as on-planter starter fertilizer systems, subsoil fertilizer applicators, or fertilizer sprayers, include: fluid system criteria sensors, such as flow sensors or pressure sensors; sensors indicating which spray head valves or fluid line valves are open; sensors associated with tanks, such as fill level sensors; sectional or system-wide supply line sensors, or row-specific supply line sensors; or kinematic sensors such as accelerometers disposed on sprayer booms. In an embodiment, examples of controllers 114 that may be used with such apparatus include pump speed controllers; valve controllers that are programmed to control pressure, flow, direction, PWM and the like; or position actuators, such as for boom height, subsoiler depth, or boom position.

In an embodiment, examples of sensors 112 that may be used with harvesters include yield monitors, such as impact plate strain gauges or position sensors, capacitive flow sensors, load sensors, weight sensors, or torque sensors associated with elevators or augers, or optical or other electromagnetic grain height sensors; grain moisture sensors, such as capacitive sensors; grain loss sensors, including impact, optical, or capacitive sensors; header operating criteria sensors such as header height, header type, deck plate gap, feeder speed, and reel speed sensors; separator operating criteria sensors, such as concave clearance, rotor speed, shoe clearance, or chaffer clearance sensors; auger sensors for position, operation, or speed; or engine speed sensors. In an embodiment, examples of controllers 114 that may be used with harvesters include header operating criteria controllers for elements such as header height, header type, deck plate gap, feeder speed, or reel speed; separator operating criteria controllers for features such as concave clearance, rotor speed, shoe clearance, or chaffer clearance; or controllers for auger position, operation, or speed.

In an embodiment, examples of sensors 112 that may be used with grain carts include weight sensors, or sensors for auger position, operation, or speed. In an embodiment, examples of controllers 114 that may be used with grain carts include controllers for auger position, operation, or speed.

In an embodiment, examples of sensors 112 and controllers 114 may be installed in unmanned aerial vehicle (UAV) apparatus or "drones." Such sensors may include cameras with detectors effective for any range of the electromagnetic spectrum including visible light, infrared, ultraviolet, near-infrared (NIR), and the like; accelerometers; altimeters; temperature sensors; humidity sensors; pitot tube sensors or other airspeed or wind velocity sensors; battery life sensors; or radar emitters and reflected radar energy detection apparatus. Such controllers may include guidance or motor control apparatus, control surface controllers, camera controllers, or controllers programmed to turn on, operate, obtain data from, manage and configure any of the foregoing sensors. Examples are disclosed in U.S. patent application Ser. No. 14/831,165 and the present disclosure assumes knowledge of that other patent disclosure.

In an embodiment, sensors 112 and controllers 114 may be affixed to soil sampling and measurement apparatus that is configured or programmed to sample soil and perform soil chemistry tests, soil moisture tests, and other tests pertaining to soil. For example, the apparatus disclosed in U.S. Pat. Nos. 8,767,194 and 8,712,148 may be used, and the present disclosure assumes knowledge of those patent disclosures.

2.4 Process Overview-Agronomic Model Training

In an embodiment, the agricultural intelligence computer system 130 is programmed or configured to create an agronomic model. In this context, an agronomic model is a data structure in memory of the agricultural intelligence computer system 130 that comprises field data 106, such as identification data and harvest data for one or more fields. The agronomic model may also comprise calculated agronomic properties which describe either conditions which may affect the growth of one or more crops on a field, or properties of the one or more crops, or both. Additionally, an agronomic model may comprise recommendations based on agronomic factors such as crop recommendations, irrigation recommendations, planting recommendations, and harvesting recommendations. The agronomic factors may also be used to estimate one or more crop related results, such as agronomic yield. The agronomic yield of a crop is an estimate of quantity of the crop that is produced, or in some examples the revenue or profit obtained from the produced crop.

In an embodiment, the agricultural intelligence computer system 130 may use a preconfigured agronomic model to calculate agronomic properties related to currently received location and crop information for one or more fields. The preconfigured agronomic model is based upon previously processed field data, including but not limited to, identification data, harvest data, fertilizer data, and weather data. The preconfigured agronomic model may have been cross validated to ensure accuracy of the model. Cross validation may include comparison to ground truthing that compares predicted results with actual results on a field, such as a comparison of precipitation estimate with a rain gauge at the same location or an estimate of nitrogen content with a soil sample measurement.

Figure 3:
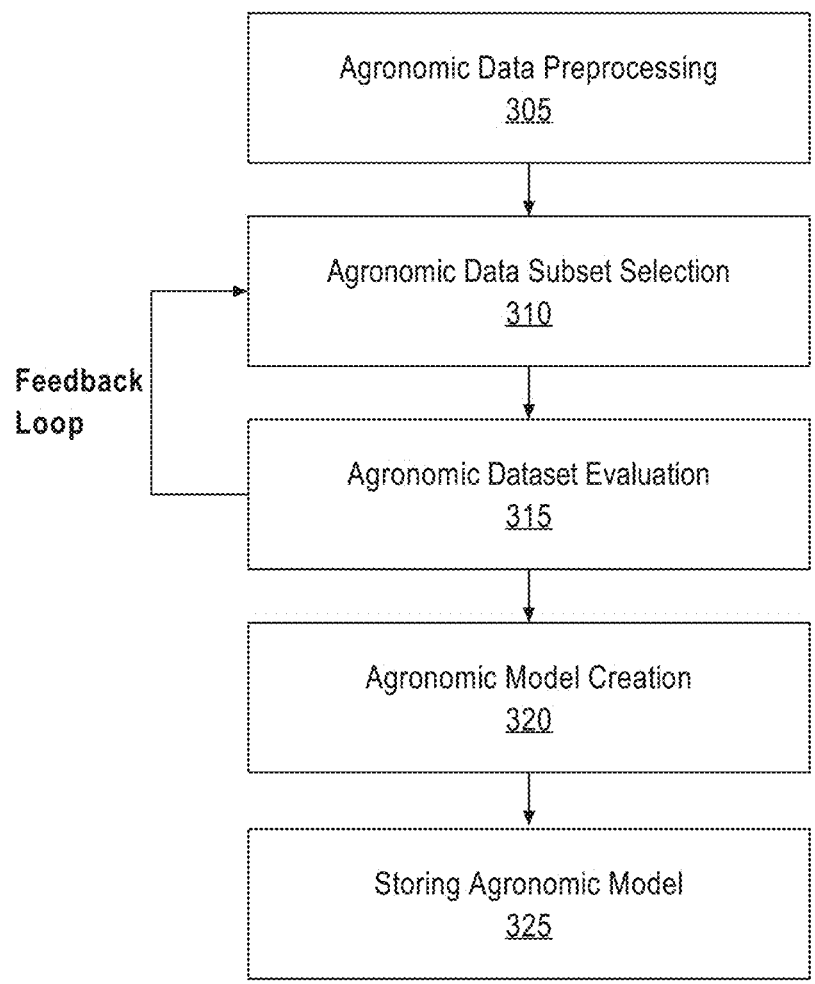
FIG. 3 illustrates a programmed process by which the agricultural intelligence computer system generates one or more preconfigured agronomic models using agronomic data provided by one or more data sources.

FIG. 3 illustrates a programmed process by which the agricultural intelligence computer system generates one or more preconfigured agronomic models using field data provided by one or more data sources. FIG. 3 may serve as an algorithm or instructions for programming the functional elements of the agricultural intelligence computer system 130 to perform the operations that are now described.

At block 305, the agricultural intelligence computer system 130 is configured or programmed to implement agronomic data preprocessing of field data received from one or more data sources. The field data received from one or more data sources may be preprocessed for the purpose of removing noise and distorting effects within the agronomic data including measured outliers that would bias received field data values. Embodiments of agronomic data preprocessing may include, but are not limited to, removing data values commonly associated with outlier data values, specific measured data points that are known to unnecessarily skew other data values, data smoothing techniques used to remove or reduce additive or multiplicative effects from noise, and other filtering or data derivation techniques used to provide clear distinctions between positive and negative data inputs.

At block 310, the agricultural intelligence computer system 130 is configured or programmed to perform data subset selection using the preprocessed field data in order to identify datasets useful for initial agronomic model generation. The agricultural intelligence computer system 130 may implement data subset selection techniques including, but not limited to, a genetic algorithm method, an all subset models method, a sequential search method, a stepwise regression method, a particle swarm optimization method, and an ant colony optimization method. For example, a genetic algorithm selection technique uses an adaptive heuristic search algorithm, based on evolutionary principles of natural selection and genetics, to determine and evaluate datasets within the preprocessed agronomic data.

At block 315, the agricultural intelligence computer system 130 is configured or programmed to implement field dataset evaluation. In an embodiment, a specific field dataset is evaluated by creating an agronomic model and using specific quality thresholds for the created agronomic model. Agronomic models may be compared using cross validation techniques including, but not limited to, root mean square error of leave-one-out cross validation (RMSECV), mean absolute error, and mean percentage error. For example, RMSECV can cross validate agronomic models by comparing predicted agronomic property values created by the agronomic model against historical agronomic property values collected and analyzed. In an embodiment, the agronomic dataset evaluation logic is used as a feedback loop where agronomic datasets that do not meet configured quality thresholds are used during future data subset selection steps (block 310).

At block 320, the agricultural intelligence computer system 130 is configured or programmed to implement agronomic model creation based upon the cross validated agronomic datasets. In an embodiment, agronomic model creation may implement multivariate regression techniques to create preconfigured agronomic data models.

At block 325, the agricultural intelligence computer system 130 is configured or programmed to store the preconfigured agronomic data models for future field data evaluation.

2.5 Implementation Example—Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

For example, FIG. 4 is a block diagram that illustrates a computer system 400 upon which an embodiment of the invention may be implemented. Computer system 400 includes a bus 402 or other communication mechanism for communicating information, and a hardware processor 404 coupled with bus 402 for processing information. Hardware processor 404 may be, for example, a general purpose microprocessor.

Computer system 400 also includes a main memory 406, such as a random access memory (RAM) or other dynamic storage device, coupled to bus 402 for storing information and instructions to be executed by processor 404. Main memory 406 also may be used for storing temporary variables or other intermediate information during execution of instructions to be executed by processor 404. Such instructions, when stored in non-transitory storage media accessible to processor 404, render computer system 400 into a special-purpose machine that is customized to perform the operations specified in the instructions.

Computer system 400 further includes a read only memory (ROM) 408 or other static storage device coupled to bus 402 for storing static information and instructions for processor 404. A storage device 410, such as a magnetic disk, optical disk, or solid-state drive is provided and coupled to bus 402 for storing information and instructions.

Computer system 400 may be coupled via bus 402 to a display 412, such as a cathode ray tube (CRT), for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane.

Computer system 400 may implement the techniques described herein using customized hard-wired logic, one or more ASICs or FPGAs, firmware and/or program logic which in combination with the computer system causes or programs computer system 400 to be a special-purpose machine. According to one embodiment, the techniques herein are performed by computer system 400 in response to processor 404 executing one or more sequences of one or more instructions contained in main memory 406. Such instructions may be read into main memory 406 from another storage medium, such as storage device 410. Execution of the sequences of instructions contained in main memory 406 causes processor 404 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 410. Volatile media includes dynamic memory, such as main memory 406. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 402. Transmission media can also take the form of acoustic or light waves, such as those generated during radio-wave and infra-red data communications.

Various forms of media may be involved in carrying one or more sequences of one or more instructions to processor 404 for execution. For example, the instructions may initially be carried on a magnetic disk or solid-state drive of a remote computer. The remote computer can load the instructions into its dynamic memory and send the instructions over a telephone line using a modem. A modem local to computer system 400 can receive the data on the telephone line and use an infra-red transmitter to convert the data to an infra-red signal. An infra-red detector can receive the data carried in the infra-red signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card, cable modem, satellite modem, or a modem to provide a data communication connection to a corresponding type of telephone line. As another example, communication interface 418 may be a local area network (LAN) card to provide a data communication connection to a compatible LAN. Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the world wide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 428, ISP 426, local network 422 and communication interface 418.

The received code may be executed by processor 404 as it is received, and/or stored in storage device 410, or other non-volatile storage for later execution.

3. Soil Testing System

Figure 7:
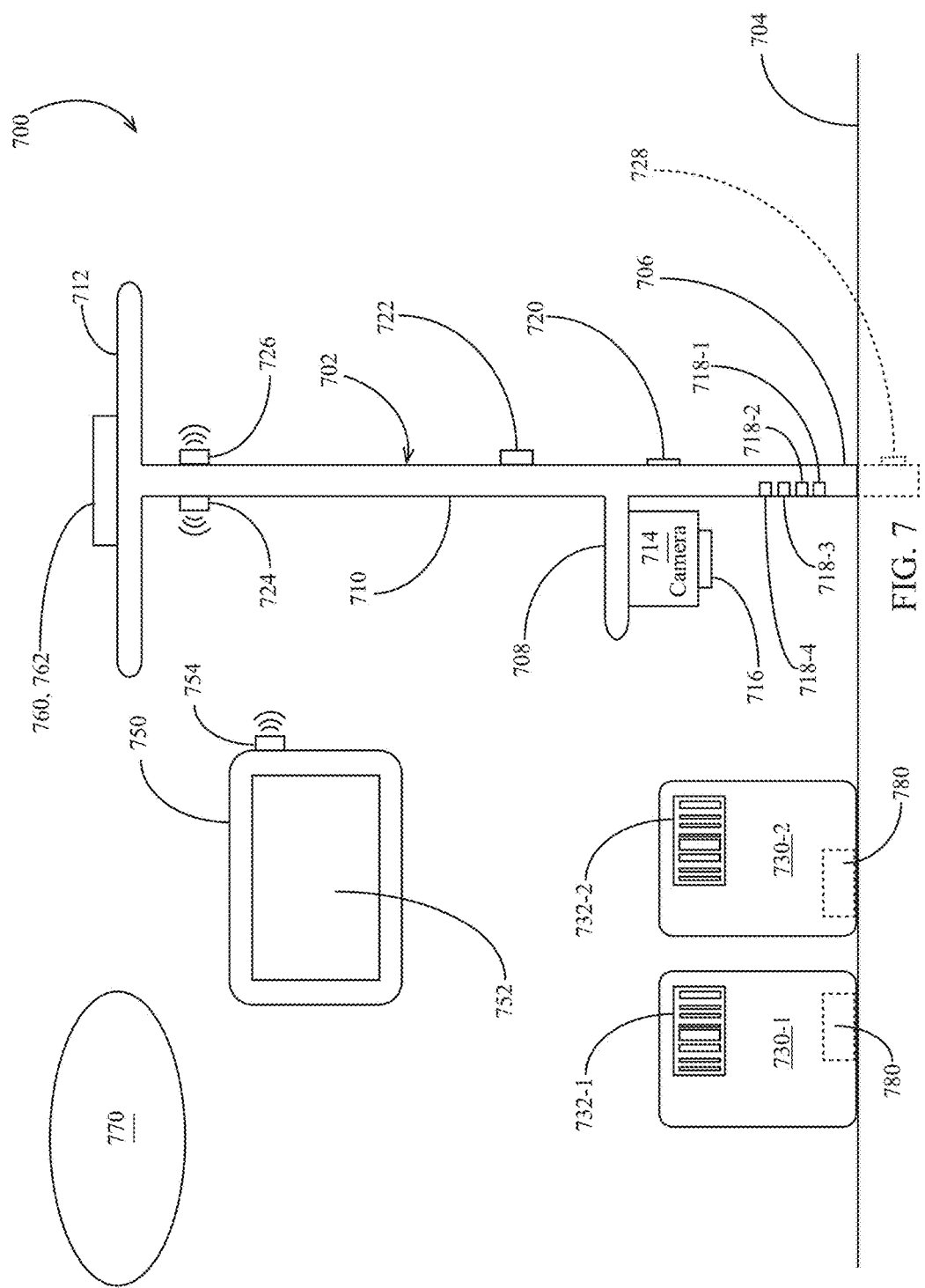
FIG. 7 illustrates an embodiment of a soil testing system.

Turning to FIG. 7, a soil testing system 700 is illustrated. The soil testing system may include a soil probe 702. The soil probe 702 may comprise a device enabling removal of soil samples 780 (for example, cylindrical core samples) from the soil 704, which may be in an agricultural field or any other location containing soil of interest; embodiments do not require use with a formally defined or specified field. The soil probe 702 may include a hollow tip portion 706 (for example, a hollow cylindrical portion) which may be configured to capture a soil sample 780 when the tip portion penetrates the soil. The tip portion may be mounted to a lower end of a central body 710 of the soil probe 702. A foothold 708 may be mounted to the central body 710 of the soil probe 702. Handlebars 712 may be mounted to an upper portion of the soil probe 702. In operation, a user may stabilize the soil probe by grasping the handlebars 712 and forces the tip portion 706 into the soil by applying a downward force on the foothold 708. In exemplary embodiments, the user captures a soil sample 780 in the tip portion 706 by twisting the probe 702 and/or by triggering a sample capture mechanism (not shown in FIG. 1) into a capture configuration in order to block the sample 780 from exiting the bottom of the tip portion 706. The user then may pull upward on the handlebars 712 to remove the probe 702 and the soil sample 780 from the soil 704. The user then may release the soil sample 780 (for example, by triggering the sample capture mechanism into a release configuration) into a container 730. The probe 702 may have common features and/or functionality (for example, the sample capture mechanism) with the probe described in U.S. Pat. No. 5,474,140, with which the reader is presumed to know and understand.

The soil testing system 700 additionally may include one or more load measurement devices 720 configured to measure a load applied to the probe 702. In some examples, the load measurement device 720 may comprise a strain gauge (for example, a Wheatstone bridge circuit) fixed to a surface of the probe 702 (for example, to an inner or outer surface of the tip portion 706 or the central body 710) and preferably oriented to measure forces applied to the probe (for example, axial forces or forces placing the probe in torsion).

The soil testing system 700 additionally may include one or more kinematic measurement devices 722 configured to measure a kinematic parameter related to the motion of the probe 702. In some examples, a kinematic measurement device 722 may comprise an accelerometer (for example, a two-axis or three-axis accelerometer). In some examples, the kinematic measurement device 722 may additionally comprise a gyroscope. The kinematic measurement device may be oriented and configured to measure acceleration, velocity and/or direction of vertical (for example, parallel with the central body 710) motion of the probe. The kinematic measurement device may be configured to measure an orientation of the probe relative to gravity.

The soil testing system 700 additionally may include one or more cameras 714. Each camera 714 may include a lens 716 facing downward (for example, toward the soil 704 in the orientation of FIG. 1). The camera 714 may capture still images and/or video. The camera 714 may measure visible light or a different range of wavelengths (for example, infrared, near-infrared) reflected from the ground surface. In some embodiments, a series of depth markers 718 are within the image capture view of the camera 714; the depth markers 718 may be arranged in vertically spaced relation along the tip portion 706 of the probe 702. Each depth marker 718 may have a color or pattern distinct from all other depth markers or from the neighboring depth marker.

Figure 10:
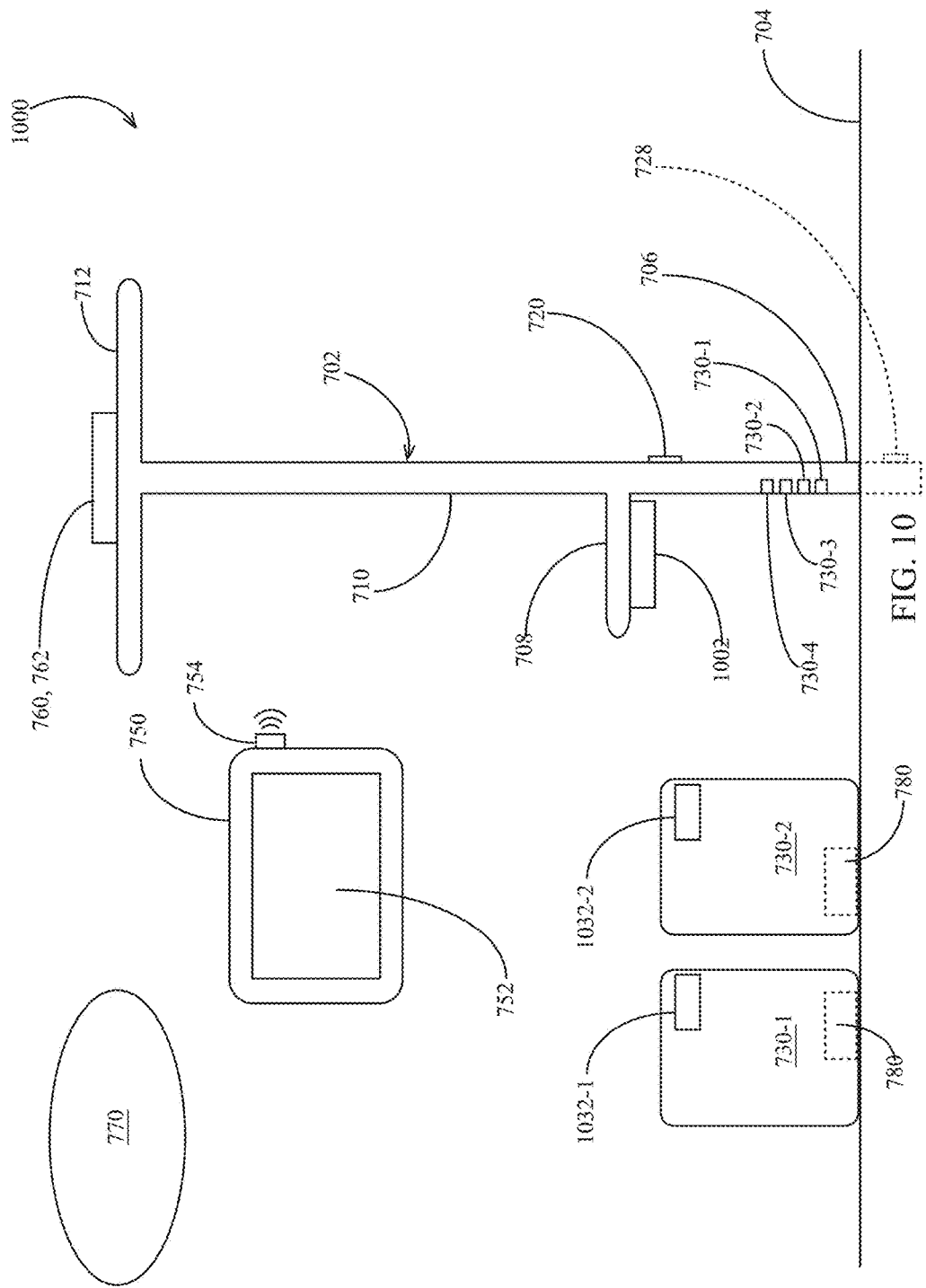
FIG. 10 illustrates another embodiment of a soil testing system.

In the system embodiment 1000 illustrated in FIG. 10, a multifunction device 1002 is mounted to the probe 702 and in data communication with the monitor 750 and/or 760. An example of device 1002 is a consumer tablet or consumer smartphone such as an Android or iPhone based smartphone. The multifunction device 1002 may include one or more of an accelerometer, a GPS receiver, a cellular modem, a wireless transmitter/receiver (for example, Bluetooth and/or WLAN), and a camera. The multifunction device 1002 may be oriented downward (in the orientation of FIG. 5) to capture images of the soil surface 704.

Referring again to the system embodiment 1000 of FIG. 5, the multifunction device 1002 (or one of the monitors 750, 160) may include a wireless communication device, for example, a near-field communication ("NFC") device. Each container 730 may include a wireless communication device 1032 affixed thereto, for example, an NFC tag. In an exemplary implementation of the embodiment 1000, the user takes a soil sample with the probe 702. The user then positions the multifunction device 1002 within a communication range of the wireless communication device (for example, by tapping the wireless communication device 1032 with the multifunction device 1002 or inherently by positioning the probe 702 to transfer the sample 780 into the container 730). Upon positioning of the multifunction device 1002 within the communication range of the wireless communication device 1032 (and/or upon entry of a data transfer command to the wireless communication device by the user), the multifunction device 1002 may transmit soil sample data to the wireless communication device. The transmitted soil sample data may comprise any one or more of the following: sample identification data (for example, geolocation data such as GPS coordinates, an image such as an image of the sample, a numerical sample identifier); soil characteristic data (for example, moisture level or soil composition measurements); and sampling quality criteria (for example, sample depth or sampling angle.

In some embodiments, the wireless communication device 1032 (such as an NFC tag) may additionally receive power from the multifunction device 1002, thus enabling the transfer and storage of data on the wireless communication device. The multifunction device 1002 may also receive soil container data (for example, a container code such as a numerical container identifier) from the wireless communication device 1032. The system 700 or another system (for example, located in a stationary soil analysis lab) may later receive the soil sample data from the wireless communication device 1032 and associate later-gathered information about the samples with the soil sample data gathered during the in-field operation. In other embodiments, other wireless communication systems and devices (for example, Bluetooth, RFID) may be employed in a similar method to that described herein.

In some embodiments, the soil testing system 700 additionally includes a soil characteristic sensor 728. The soil characteristic sensor may comprise components configured to measure one or more characteristics of the soil; for example, a thermocouple for measuring soil temperature, a capacitive probe for measuring soil moisture, a pair of electrodes for measuring soil electrical conductivity, and/or a reflectivity sensor for measuring reflectivity of the soil (for example, at one or more wavelengths in the infrared and/or infrared spectrum). The soil testing system 700 may comprise a plurality of soil characteristic sensors 728 disposed at a plurality of vertical positions along the tip portion 706 such that the soil characteristics described above may be measured at a plurality of depths along the soil sample 780. In some embodiments, the soil characteristic sensor 728 is disposed to measure soil characteristics of the soil surrounding the soil (for example, exposed to soil radially outward of the tip portion 706); in other embodiments, the soil characteristic sensor is disposed to measure soil characteristics of the soil sample 780 within the tip portion 706.

The soil testing system 700 may include a monitor including a memory, processor and graphical user interface ("GUI"). Referring again to FIG. 1, the monitor may be a probe-mounted monitor 760 having a GUI 762. In other embodiments, the monitor may alternatively or additionally comprise a mobile monitor 750 having a GUI 752. The mobile monitor 750 may comprise a tablet computing device.

The soil testing system 700 may be in data communication with the Internet 770 via any appropriate device or devices and transfers data (for example, images, sensor data) to remote server via the Internet. The probe-mounted sensors (for example, the camera 714, kinematic measurement devices 722, the soil characteristic sensors 728, load measurement devices 720) may be in data communication with the monitors 750, 160 and with the Internet 770 by any appropriate device or devices. In some embodiments, the probe-mounted monitor 760 is in electrical communication with the probe-mounted sensors. In some embodiments, the probe-mounted sensors are in electrical communication with a cellular modem 724 or other data transfer device which is in data communication with the Internet. In some embodiments, the probe-mounted sensors are in electrical communication with a wireless transmitter/receiver 726 (for example, a WLAN transmitter/receiver). The wireless transmitter/receiver 726 may be in data communication with a wireless transmitter/receiver 754 (for example, a WLAN transmitter/receiver) of the mobile monitor 750. The mobile monitor 750 may include a cellular modem or other data transfer device in data communication with the Internet.

Figure 8:
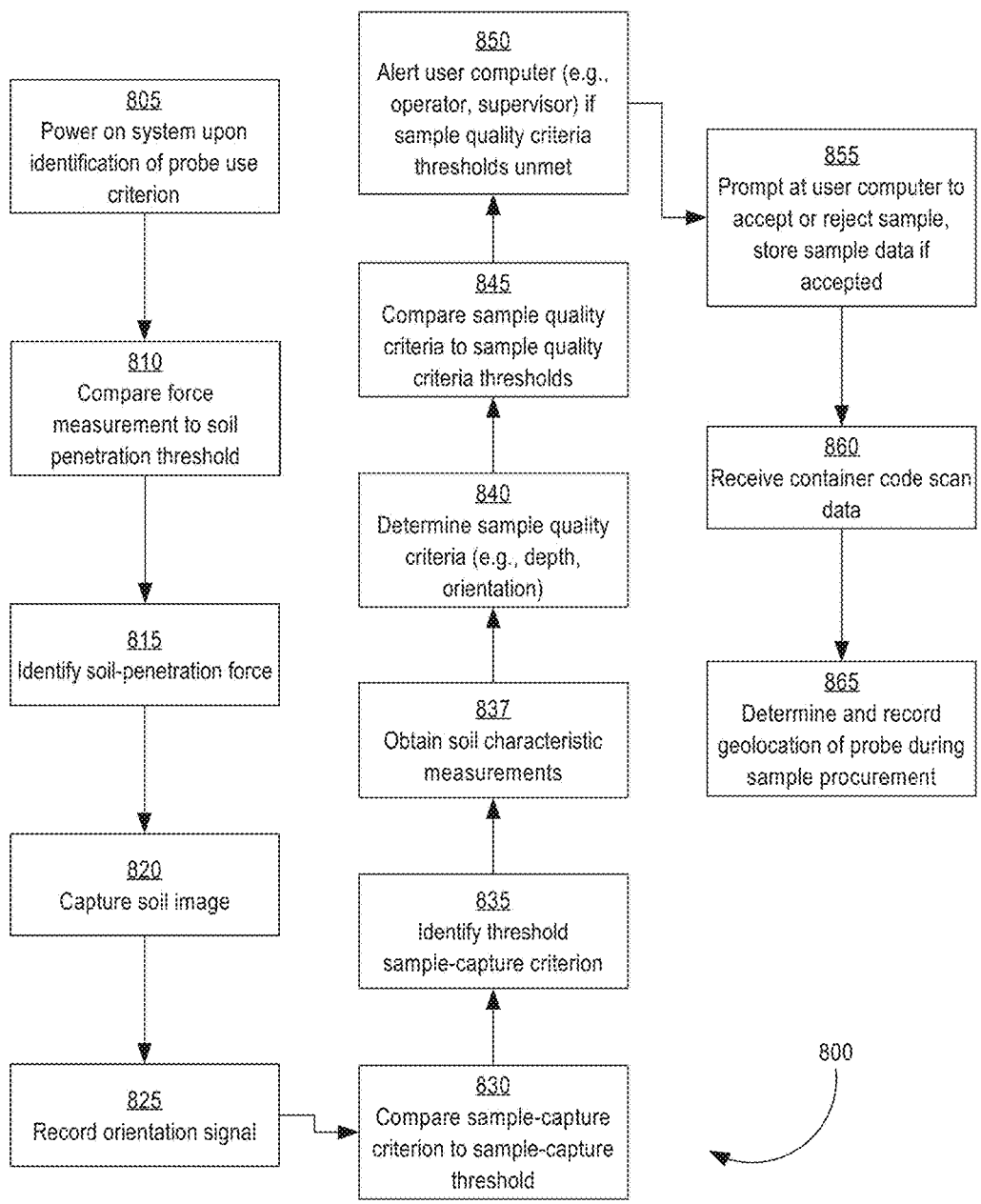
FIG. 8 illustrates an exemplary soil testing process.

Turning to FIG. 8, an exemplary process 800 for monitoring a soil testing system is illustrated.

Prior to step 805, the system 700 may be in a low-power state in which only a subset of the components of the system 700 (for example, the monitor, the kinematic measurement device, and/or the load measurement device) receive power. At step 805, the monitor may identify a probe use criterion. The probe use criterion may comprise a threshold value measured by the kinematic measurement device, for example, a signal within a signal range corresponding to a vertical orientation of the probe 702. The probe use criterion may also comprise a threshold value measured by the load measurement device, for example, a signal within a signal range corresponding to a soil-sampling force. Upon identifying a probe use criterion, the system 700 may enter a full-power state in which all or a more inclusive subset of the components of the system 700 receive power.

At step 810, the system 700 may compare a force measurement (for example, a signal generated by the load measurement device) to a threshold value. In some embodiments, the signal generated by the load measurement device 720 is compared to a soil penetration threshold, for example, a value empirically determined to correspond to an axial force (for example, a downward force when the probe is in a vertical orientation) sufficient to drive the soil probe into the soil. The threshold value used at step 810 may in some embodiments be set lower than the empirically soil penetration threshold, for example, 50% of the soil penetration threshold. It should be appreciated that the force measured by the load measurement device 720 is (in the embodiment of FIG. 1) related to the force applied by the user to the probe (for example, to the handlebars 712 and/or the foothold 708). In some embodiments, the load measurement may be used to estimate a soil compaction and associated with the GPS-reported location and/or the corresponding depth (said depth being measured as described herein).

At step 815, the system 700 may identify a soil-penetration force, for example, by determining that the signal generated by the load measurement device 720 meets or exceeds the threshold value of step 810.

At step 820, upon identifying a soil-penetration force, the system 700 may capture a soil image. In some embodiments, the soil image is captured by the camera 714. In the embodiment of FIG. 1, the camera lens 716 is oriented downward (when the probe 702 is in a vertical orientation) such that the image captured by the camera includes a region of soil which may be adjacent to and/or surrounding the location at which the probe tip portion 706 enters the soil surface 704. In some embodiments, the camera 714 is also disposed to capture an image including the depth markers 718. In some examples, if the probe is not inserted in the soil the image captured at step 820 includes all of the depth markers 718. It should be appreciated that as the probe tip portion 706 is inserted deeper into the soil surface 704, a subset of depth markers 718 will be covered by the soil and not included in the image captured at step 820.

Figure 11B:
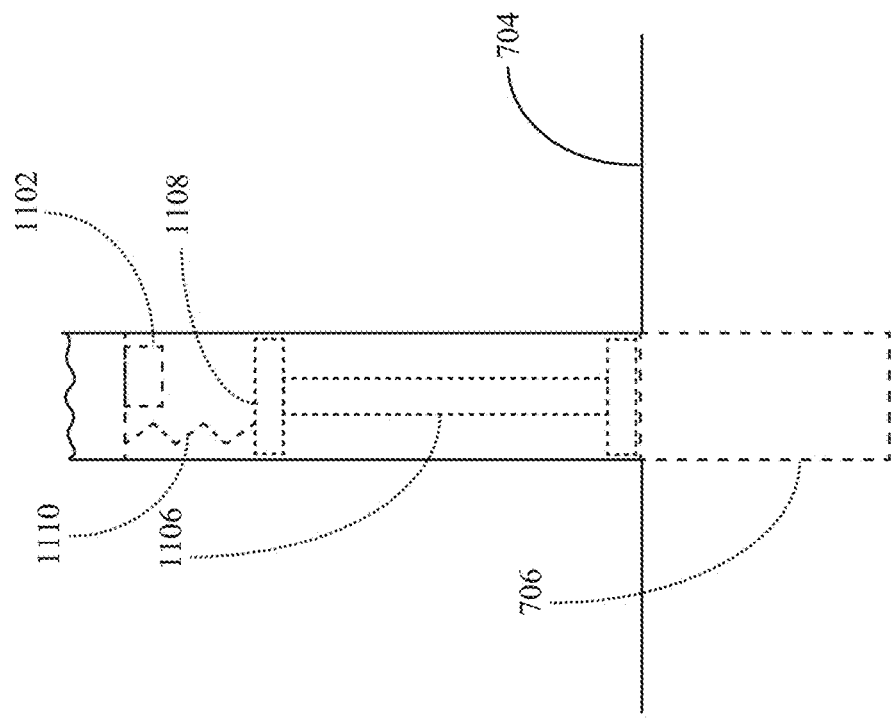
FIG. 11B illustrates another embodiment of a soil probe having an interior depth sensor.
Figure 11A:
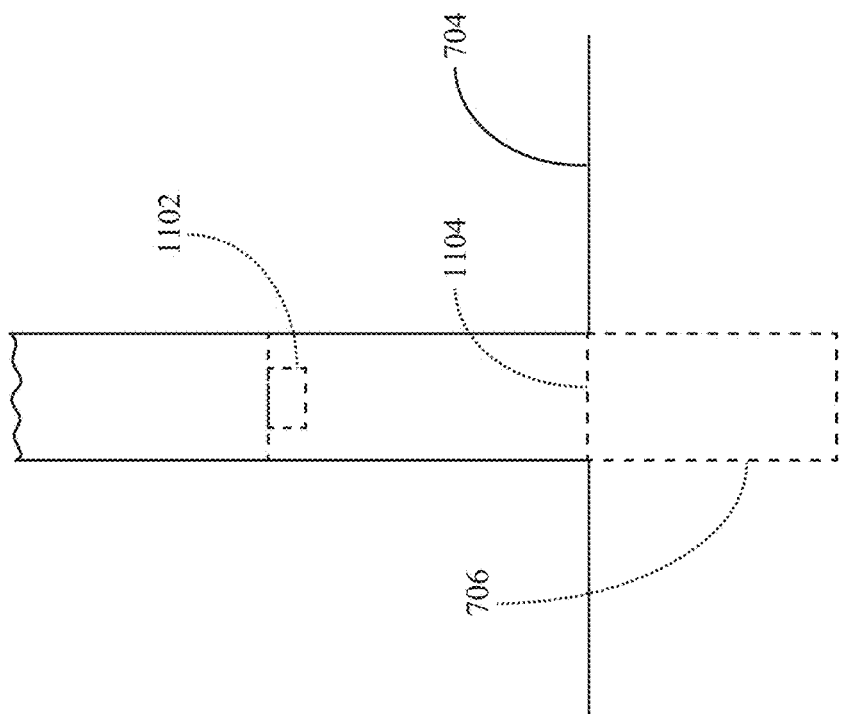
FIG. 11A illustrates a further soil probe having an interior depth sensor.

In some embodiments, the sample depth may be additionally or alternatively determined by a proximity sensor (for example, a laser or ultrasound proximity sensor) mounted to the probe and oriented to measure a distance between the sensor and the ground surface; in embodiments including a laser proximity sensor, a wear-resistant lens (for example, sapphire) may be disposed over the sensor and may isolate the sensor from atmospheric dust and residue. In some embodiments, the proximity sensor may comprise a sonar sensor. In some such embodiments, the proximity sensor may be mounted to the bottom of the foothold 708 and oriented downward when the probe 702 is in the upright position. In other such embodiments such as those illustrated in FIG. 11A and FIG. 11B, a proximity sensor 1102 may be mounted in an interior volume of the probe 702 and disposed to measure a distance to an upper surface 1104 of soil captured in the hollow tip portion 706 to form the soil sample; it should be appreciated that as the hollow tip portion 706 is extended deeper into the soil, the upper surface 1104 becomes closer to the proximity sensor 1102. In a modified embodiment, the proximity sensor 1102 instead measures the distance between itself and an upper surface 1108 of a piston 1106 which is displaced upward as the soil sample is captured by the hollow tip portion 706; a spring 1110 may eject the sample and returns the piston 1106 to a non-deflected position. The proximity sensor may be in data communication for sending proximity signals to one or both of the monitors 750, 160. The monitors 750, 160 may be configured to estimate the sample depth based on the proximity signals and/or the camera images.

At step 825, the system 700 may record an orientation signal (for example, a signal generated by the kinematic measurement device 722) corresponding to a time of soil sample capture. For example, the system 700 may record the orientation signal upon identifying a soil-penetration threshold.

At step 830, the system 700 may compare a sample-capture criterion (for example, a measured force; a measured kinematic parameter such as motion, velocity or acceleration; or a time period elapsing after the soil-penetration threshold is met) to an associated sample-capture threshold (for example, a force threshold such as 5, 10, 20, 50 or 100 Newtons; a kinematic threshold such as an upward motion, velocity or acceleration greater than 0; or a time period corresponding to an empirically determined representative sample capture time such as 1, 2, 3, 4, or 5 seconds). At step 835, the system 700 may identify that the sample-capture criterion has met or exceeded the threshold value; the system 700 may carry out steps 837 and 240 (described below) upon making this threshold criterion.

At step 837, upon identifying a threshold sample-capture criterion, the system 700 obtains soil characteristic measurements using the soil characteristic sensors 728. The system 700 prompts the user to hold the probe in a stationary position at full sample depth while the soil characteristic measurements are taken.

At step 840, the system 700 may determine one or more sample quality criteria and at step 845 compares those sample quality criteria to one or more associated sample quality thresholds. In some embodiments, the sample quality criterion may comprise orientation of the soil probe 702 and the associated sample quality threshold may comprise a range of orientations within a threshold (for example, 10 degrees) of vertical. In some embodiments, the sample quality criterion may comprise an estimated sample depth (for example, based on a vertical downward distance moved prior to a change in direction upon retraction of the probe 702 from the soil, based on a proximity signal, or based on a camera image including one or more depth markers) and the sample quality threshold may comprise a desired sample depth (for example, a desired sample depth in the range between 3 to 18 inches). The sample quality criteria may be identified based on sensor signals transmitted upon the identification of a threshold sample-capture criterion in step 835 and/or within a time period (for example, 500 milliseconds or 1 second) prior to or following such identification.

At step 850, the system 700 may alert the user computer (for example, through a monitor graphical user interface on the device or a remote supervisor computer) if the sample criteria thresholds are unmet.

At step 855, regardless of whether the sample criteria thresholds are met or unmet, the system 700 may prompt at the user computer to reject or accept the sample. If the user accepts the sample (or in some embodiments if the user does not reject the sample within a threshold time) the system 700 may store the sample data (for example, sample quality criteria) and associates them with a unique sample identifier (for example, an alphanumeric identifier) associated with the sample.

At step 860, the operator (in some embodiments prompted by an alert on the graphical user interface) may scan a container code 732 (for example, a bar code such as a Quick Response Code) on one of the containers 730. The container code 732 may be scanned using the camera 714 or with a camera and associated code-reading software on the monitor 750. The system 700 may receive the container code and associates it with the unique sample identifier.

At step 865, the system 700 may determine and records the geo-location (for example, GPS coordinates) of the probe 702 during the sample procurement and associates the geo-location with the unique sample identifier. The geo-location may be identified using a GPS receiver, for example, a GPS receiver housed in the monitor 750 or the monitor 760. The system 700 may generate and display a sample map of the geo-locations of each sample stored. The sample map may include field and management zone boundaries defined by the user and/or the system 700. The system 700 may additionally monitor one or more signals generated by the kinematic sensor or sensors 145 between identification of a first sample (for example, identified based on a first load measurement, kinematic measurement or user input) and identification of a second sample (for example, identified based on a first load measurement, kinematic measurement or user input) in order to estimate the distance between the first and second samples in the horizontal plane of the field being sampled; it should be appreciated that the GPS receiver signal may also be monitored to estimate the same distance between samples.

With respect to the exemplary process 800 described herein, when a step is carried out by the system 700 it may be carried out by one of the monitors 750, 760 and/or a remote computer.

In some embodiments, the system 700 may take certain actions or enter certain modes based on a kinematic measurement (made either by a dedicated kinematic measurement device 722 or by a kinematic measurement device incorporated in a multifunction device 1002 as described herein) resulting from a motion pattern of the probe 702 (and/or multifunction device 1002) caused by the user. As illustrative examples, the system 700 may take one or more actions (for example, scanning a container code, powering on or off, associating subsequently gathered data with a new sample) upon recognizing a motion pattern (for example, shaking up and down along a vertical axis a plurality of times). The system 700 may communicate to the user (for example, by an audible or visual alert) that the motion pattern has been recognized and/or that the desired action has been taken.

Figure 9:
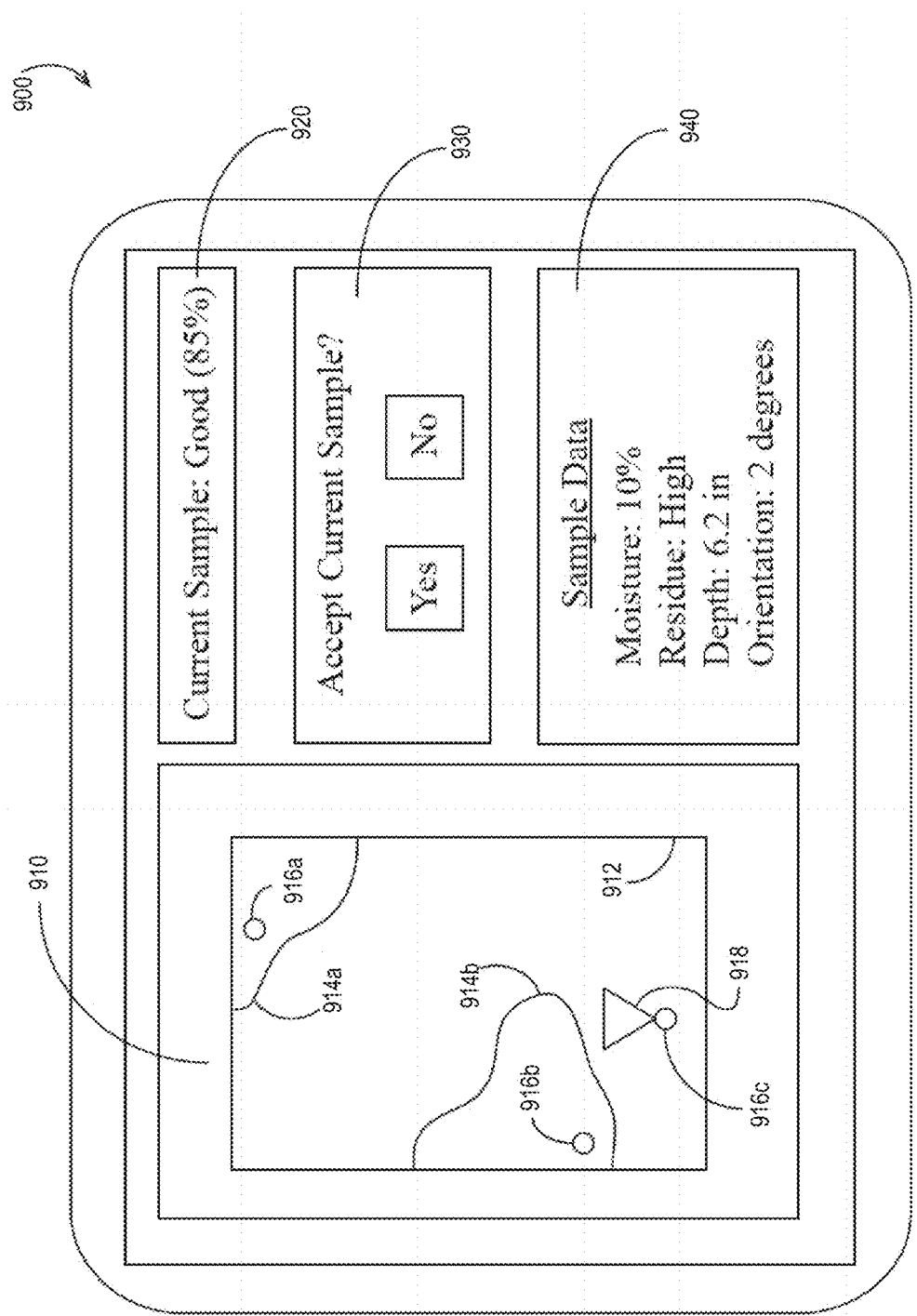
FIG. 9 illustrates an exemplary graphical user interface screen for soil testing.

Turning to FIG. 9, an exemplary graphical user interface screen 900 is illustrated. The GUI screen 900 may be displayed on the GUI of one or more of the monitors 750, 760 (which may comprise touch-screen interfaces) or a remote computing device.

The GUI screen 900 may include a map 910 including a field boundary 912, management zone boundaries 914, and previously captured sample locations 916. An annotation 918 may mark the current location of the probe. The management zone boundaries 914 may be defined by the user or system 700. In some embodiments, the management zone boundaries 914 delimit regions of the field that have similar characteristics (for example, past yield, elevation, slope, tiling, soil type) and/or regions of the field having a common agricultural management criterion (for example, seed planting rate, hybrid type, fertilizer application).

The GUI screen 900 may include a sample quality indicator window 920. The sample quality indicator window 920 may include a verbal or numeric description of the sample quality of the most recently captured sample. The description may be based on the sample quality criteria discussed above. In one example, a numerical description comprises the sample quality criterion divided by the sample quality threshold (for example, expressed as a percentage). In some examples, a verbal description indicates the sample quality is "Good" if the numerical description meets or exceeds a threshold (for example, 80%) and "Poor" if the numerical description is less than that threshold.

The GUI screen 900 may include a sample rejection interface window 930 enabling the user to accept or reject a sample by selecting "Yes" or "No", respectively. If the sample is accepted, the sample data (for example, sample quality, soil characteristics, and geo-location) may be stored and associated with the unique sample identifier.

The GUI screen 940 may include a sample data window 940 displaying sample data (for example, moisture, residue level, depth, orientation) for the current (for example, most recently captured) sample. In some embodiments, selecting (for example, tapping or clicking) of samples 916 other than the current samples causes the sample data and/or the sample quality to be updated to represent the values associated with the selected sample.

Components described herein as being in electrical communication may be in data communication via any suitable device or devices. The term "data communication" as used herein is intended to encompass wireless (for example, radio-based), electrical, electronic, and other forms of digital or analog data transmission. Components described herein as being in communication via a harness may be in data communication via any suitable device or devices. A harness may comprise a single electrical line or a bundled plurality of electrical lines, and may comprise a point-to-point connection or a bus.

The monitors 750, 760 and any remote servers and computing devices referenced herein may comprise non-transitory computer-readable media. As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

What is claimed is:

1. A method for soil testing, comprising:
    positioning a soil probe above a region of soil;
    applying a force to the soil probe to cause the soil probe to obtain a soil sample, the soil sample extending a first depth into soil in the region of soil;
    using a computing device communicatively coupled to the soil probe, determining a soil sample quality criterion for the soil sample;
    determining whether the force exceeds a threshold;
    in response to determining that the force exceeds the threshold, determining a location of the region of the soil using a global positioning receiver of the computing device; and
    associating, in digital storage of the computing device, an identifier of the soil sample with the soil sample quality criterion.

2. The method of claim 1, wherein the step of determining a soil sample quality criterion comprises measuring the first depth.

3. The method of claim 1, further comprising:
    using the computing device, determining whether the force exceeds a threshold; and
    upon determining that the force exceeds the threshold, automatically obtaining a photographic image of the region using a camera communicatively coupled to the computing device.

4. The method of claim 1, wherein the step of determining a soil sample quality criterion comprises measuring an angle of orientation of the soil probe.

5. The method of claim 1, further comprising automatically obtaining a photographic image of the region of soil using a camera communicatively coupled to the computing device.

6. The method of claim 1, further comprising determining a location of the region of the soil using a global positioning receiver of the computing device.

7. The method of claim 1, further comprising:
    using the computing device, obtaining a soil characteristic measurement; and associating, in digital storage of the computing device, the identifier of the soil sample with the soil characteristic measurement.

8. The method of claim 1, further comprising:
transferring the soil sample to a container; and
associating, in digital storage of the computing device, the identifier of the soil sample with the container.

9. The method of claim 8, wherein the step of associating the identifier of the soil sample with the container comprises:
receiving a container code; and
associating the container code with the identifier of the soil sample.

10. The method of claim 9, wherein the container code is scanned from the container.

11. The method of claim 9, wherein the container code is stored on a near-field communication device.

12. The method of claim 1, further comprising:
transferring the soil sample to a container; and
transmitting soil sample data to a wireless communication device affixed to the container.

13. The method of claim 12, wherein the wireless communication device comprises a near-field communication device.

14. The method of claim 12, wherein the soil sample data comprises one of the soil sample quality criterion, sample identification data, and soil characteristic data.

15. A soil testing system, comprising:
a soil probe having a hollow portion for receiving a soil sample;
a computing device communicatively coupled to the soil probe, wherein the computing device is programmed to monitor a force applied to the soil probe and determine whether the force exceeds a threshold;
a soil sample quality measurement device; and
a computer system in data communication with the soil sample quality measurement device, wherein the computer system is programmed to associate the soil sample with a soil sample quality criterion.

16. The soil testing system of claim 15, wherein the soil sample quality measurement device comprises a depth measurement device.

17. The soil testing system of claim 16, wherein the depth measurement device comprises a proximity sensor mounted to the probe, the proximity sensor disposed to measure a distance between the proximity sensor and a soil surface engaged by the soil probe.

18. The soil testing system of claim 16, wherein the depth measurement device comprises a camera, wherein the camera is disposed to capture an image of a depth marker affixed to the soil probe.

19. The soil testing system of claim 15, further comprising an orientation measurement device in data communication with the soil testing system, wherein the orientation measurement device generates a signal related to an orientation of the soil probe with respect to vertical.

20. A method for soil testing, comprising:
positioning a soil probe above a region of soil;
applying a force to the soil probe to cause the soil probe to obtain a soil sample, the soil sample extending a first depth into soil in the region of soil;
using a computing device communicatively coupled to the soil probe, determining a soil sample quality criterion for the soil sample;
determining whether the force exceeds a threshold;
in response to determining that the force exceeds the threshold, determining a location of the region of the soil using a global positioning receiver of the computing device and automatically obtaining a photographic image of the region using a camera communicatively coupled to the computing device; and
associating, in digital storage of the computing device, an identifier of the soil sample with the soil sample quality criterion.

* * * * *